US011896687B1

(12) United States Patent
Leverenz et al.

(10) Patent No.: US 11,896,687 B1
(45) Date of Patent: Feb. 13, 2024

(54) OLEOGEL HAVING A PROTEIN MICROSTRUCTURE WITH OPTIMIZED OIL RELEASE PROPERTIES FOR REPLACING STRUCTURED FATS AND SATURATED OILS IN FOOD AND COSMETIC PRODUCTS

(71) Applicant: Shiru, Inc., Alameda, CA (US)

(72) Inventors: Ryan Leverenz, Kensington, CA (US); Carl Atik, Richmond, CA (US); Alina Kim, San Francisco, CA (US); Elizabeth Kirk, Alameda, CA (US); Yamile Mennah-Govela, Oakland, CA (US); Janelle Myers, Berkeley, CA (US); Jason Voogt, LaFayette, CA (US)

( * ) Notice: Subject to any disclaimer, the term of this patent is extended or adjusted under 35 U.S.C. 154(b) by 0 days.

(21) Appl. No.: 18/199,974

(22) Filed: May 22, 2023

(51) Int. Cl.
    *A61K 8/04*     (2006.01)
    *A61K 8/92*     (2006.01)
    (Continued)

(52) U.S. Cl.
    CPC ............. *A61K 8/042* (2013.01); *A21D 2/165* (2013.01); *A21D 2/264* (2013.01); *A23C 20/00* (2013.01);
    (Continued)

(58) Field of Classification Search
None
See application file for complete search history.

(56) References Cited

U.S. PATENT DOCUMENTS 2,914,962 A    12/1959   Schmidt
8,796,342 B2 *   8/2014   Savin .................. A23D 7/0056
                                                            510/513

(Continued)

FOREIGN PATENT DOCUMENTS

CN         113261594 A      8/2021
CN         114190443 A      3/2022
(Continued)

OTHER PUBLICATIONS

Feichtinger et al ("Protein Oleogels prepared by Solvent Transfer Method with Varying Protein Sources", Food Hydrocolloids, vol. 132 (2022), 107821 (p. 1-10) (Year: 2022).*

(Continued)

*Primary Examiner* — Sin J Lee
(74) *Attorney, Agent, or Firm* — MS IP Law

(57) ABSTRACT

This disclosure provides a protein oleogel comprising plant protein dispersed in a liquid oil phase. The oleogel has a microstructure in the form of fibrils, sheets, or other particles with a high aspect ratio that are substantially not interconnected. It can be manufactured by a process that includes solubilizing and denaturing the protein in an aqueous liquid, flash freezing and drying the protein, and then gradually and gently adding a suitable oil or oil mixture. The protein microstructure releases some but not all of the oil when heated. The oleogel forms a spreadable emulsion in an aqueous liquid that is stable for at least six weeks without evidence of creaming. The oleogel may substitute for oils and fats of animal origin in food, food ingredients, cosmetics, and personal care products. This lessens the impact of food manufacturing on the environment, which helps mitigate climate change.

17 Claims, 14 Drawing Sheets

(51) Int. Cl.

| | | |
|---|---|---|
| A61Q 17/04 | (2006.01) | |
| A61Q 19/00 | (2006.01) | |
| A61Q 19/08 | (2006.01) | |
| A23D 9/00 | (2006.01) | |
| A23D 9/007 | (2006.01) | |
| A23D 9/02 | (2006.01) | |
| A23D 9/04 | (2006.01) | |
| A23D 9/05 | (2006.01) | |
| A21D 2/16 | (2006.01) | |
| A21D 2/26 | (2006.01) | |
| A23C 20/00 | (2006.01) | |
| A23C 20/02 | (2021.01) | |
| A23G 9/32 | (2006.01) | |
| A23G 9/38 | (2006.01) | |
| A23J 3/14 | (2006.01) | |
| A23J 3/16 | (2006.01) | |
| A23J 3/22 | (2006.01) | |

(52) U.S. Cl.
CPC ............... *A23C 20/02* (2013.01); *A23D 9/00* (2013.01); *A23D 9/007* (2013.01); *A23D 9/02* (2013.01); *A23D 9/04* (2013.01); *A23D 9/05* (2013.01); *A23G 9/327* (2013.01); *A23G 9/38* (2013.01); *A23J 3/14* (2013.01); *A23J 3/16* (2013.01); *A23J 3/227* (2013.01); *A61K 8/922* (2013.01); *A61Q 17/04* (2013.01); *A61Q 19/00* (2013.01); *A61Q 19/08* (2013.01); *A61K 2800/412* (2013.01); *A61K 2800/5922* (2013.01)

(56) References Cited

U.S. PATENT DOCUMENTS

| | | |
|---|---|---|
| 8,940,354 B2 | 1/2015 | Marangoni |
| 9,655,376 B2 | 5/2017 | Ergun |
| 10,874,115 B2 | 12/2020 | Perez Gallardo |
| 11,439,159 B2 | 9/2022 | Hume |
| 11,653,671 B2 | 5/2023 | Beekmans |
| 2022/0295811 A1 | 9/2022 | Scholten |

FOREIGN PATENT DOCUMENTS

| | | | |
|---|---|---|---|
| EP | 3011836 A1 | 10/2014 | |
| NL | 2027755 B2 | 10/2022 | |
| WO | WO 2016/062685 | 4/2016 | |
| WO | WO-2016062685 A1 * | 4/2016 | ............. A21D 13/08 |
| WO | WO 2022/031172 | 2/2022 | |

OTHER PUBLICATIONS

S. Chakroborty. Next generation protein rich potato see protein gene AmA1. Proc. Natl. Acad. Sci. 107:17533, Oct. 12, 2010.
A. De Vries. Effect of oil type on network formation by protein aggregates into oleogels. RSC Adv. 7:11803, Feb. 7, 2017.
A. Feichtinger. Protein oleogels prepared by solvent transfer method. Food Hydrocolloids 132:107821, Nov. 1, 2022.
A. Feichtinger. Preparation of protein oleogels. Foods 9:1745, Nov. 1, 2020.
M. Gibis. Influence of the protein content on fiber morphology. Appl. Sci. 11:7896, Aug. 27, 2021.
S. Manzoor. Oleogels for the development of healthy meat products. Appl. Food Res. 2:100212, Aug. 22, 2022.
T. Nicolai. Controlled food protein aggregation. Curr. Opin. Colloid Interface Sci. Aug. 1, 2013.
C. Park. Critical review of oleogels in food. Frontiers Sustainable Food Sys. 4:139, Sep. 15, 2020.
A. Puscas. Oleogels in food. Foods 9:70, Jan. 8, 2020.
A. Puscas. Application of analytica methods for analysis of oleogels. Polymers 13:194, Jun. 10, 2021.

E. Scholten. Edible oleogels: how suitable are proteins as a structurant? Curr. Op. Food Sci. 27:36, May 11, 2019.
J.S. Shaun Yong. Plant proteins for future foods. Foods 10:1967, Aug. 23, 2021.
S. Sivakanthan. Synergistic effects of oleogelators in taloring properties of oleogels. Compr. Rev. Food Sci. Food Suf. 21:3507, Apr. 10, 2022.
M. Wu. Rheology and microstructure of myofibrillar protein olive oil composite gels. J Sci Food Agric. DOI 10.1004/sfa.8528. Jul. 5, 2017.
A.K. Zetzy. Microstructure and mechanical properties of ethylcellulose oeogels. Ph.D. thesis, Nov. 1, 2013.
Akgonullu et al: Review of Similarities and Difference in Behaviour in Bulk Phases and at Interfaces. Advances in Colloid and Interface Science Oct. 1, 2023, 320, 102983.
Andlinger et al.: Microstructures of Potato Protein Hydrogels and Aerogels Produced by Thermal Crosslinking Food Hydrocolloids Sept 1, 2020, 112, 106305.
Chung Reduced Calorie Emulsion-Based Foods: Protein Microparticles and Dietary Fiber as Fat Replacers. Food Research International Jan. 1, 2014, 64, 664-67.
Dickinson, E. Biopolymer-Based Particles as Stabilizing Agents for Emulsions and Foams. Food Hydrocolloids Jan. 1, 2017, 68, 219-231.
Guo, Oleogels/Emulsion Gels as Novel Saturated Fat Replacers in Meat Products: Food Hydrocolloids Apr. 1, 2023, 137, 108313.
Herneke. Protein Nanofibrils for Sustainable Food-Characterization and Comparison of Fibrils ACS Food Sci. Techno May 14, 2021, 1 (5), 854-864.
Ipsen Whey Proteins for Improving Dairy Product Texture. International Dairy Journal Apr. 1, 2017, 67, 73-79.
Kew et al.: Transforming Sustainable Plant Proteins into High Performance Lubricating Microgels. Nat Commun Aug. 7, 2023, 14 (1), 4743.
Manzocco, et al:. Aerogels as Porous Structures for Food Applications: Food Structure Feb. 1, 2021, 28, 100188.
Manzoor Promising Alternatives to Solid Fats for Food Applications. Food Hydrocolloids for Health Dec. 1, 2022, 2, 100058.
Mohanan. Oleogelation Using Pulse Protein-Stabilized Foams and Their Potential RSC Adv. Mar. 1, 2020, 10 (25), 14892-14905.
Nasrollahzadeh. Dispersion of Low Concentration of Particulate or Fibrillated Protein Fillers. Food Hydrocolloids Nov. 1, 2023, 144, 108985.
Rezaee Canola Protein Microgel as a Potential Animal Fat Replacer. ACS Food Sci. Technol. Oct. 11, 2022, 2 (10), 1681-1690.
Shen et al: From Protein Building Blocks to Functional Materials. ACS Nano Mar. 24, 2021, 15 (4), 5819-5837.
Silva-Avellaneda Effect of Composition, Microfluidization and Process Parameters on Formation of Oleogels Sci Rep Mar. 30, 2021, 11 (1), 7161.
Vélez-Erazo Protein-Based Strategies for Fat Replacement: Approaching Different Protein Colloidal Types Food Research International May 7, 2022, 156, 111346.
Zhang. Heat Stability and Rheological Properties of Composite Microparticle Dispersions. Food Hydrocolloids Mar. 1, 2020, 100, 105449.
Zhang Protein Nanoparticles for Pickering Emulsions: A Comprehensive Review on Their Shapes, Preparation Methods, and Modification Trends in Food Science & Technology July 1m vol. 113 (2021) p. 26-41.
De Vries. Protein oleogels from heat set whey protein. J Colloid Interface Sci 286:75-83, Jan. 1, 2017.
De Vries. Conrolled agglomeration of protein aggregates in liquid oil. ACS Appl Mater Interfaces 9:10136, Jan. 1, 2017.
De Vries. Tuning protein-based oleogels by water addition and heat treatment. Food Hydrocolloids 29:100-109, Jan. 1, 2018.
Protein oleogels from protein hydrogels via a stepwise solvent exchange route. Auke de Vries et al., Langmuir. Dec. 29, 2015;31(51): 13850-9.
Controlling agglomeration of protein aggregates for structure formation in liquid oil: A Sticky Business. Auke de Vries et al., ACS Appl. Mater. Interfaces 2017, 9, 11, 10136.

(56) References Cited

OTHER PUBLICATIONS

Structural characterization of oleogels from whey protein aerogel particles. S. Plazzotta et al., Food Res Int. Jun. 2020; 132:109099.
Structural characterisation and absorption capability of whey protein aerogels obtained by freeze-drying or supercritical drying. L. Manzocco et al., Food Hydrocolloids, vol. 22 (2022) 107117.
Formation of protein oleogels via capillary attraction of engineered protein particles. S.-S. Wang et al., Food Hydrocolloids, vol. 133, Dec. 2022, 107912.
Feichtinger. Protein oleogels prepared by solvernt transfer. Food Hydrocoloids 132:107821 (May 28, 2022).

\* cited by examiner

Ref. (A)

Ref. (B)

Ref. (C)

Ref. (D)

Ref. (E)

Ref. (F)

Panel A
*fibrils*

| Structure outline | Isolated outline | Idealized linear structure |
|---|---|---|
|  |  |  |

T1, L1 = 2.5 um, 16.0 um
T2, L2 = 1.8 um, 15.6 um
T3, L3 = 3.0 um, 6.7 um
T4, L4 = 2.5 um, 1.9 um
Avg. Thickness = 2.5 um, Max. Length = 25 um
Aspect ratio = 24 / 2.5 = 10

| | | |
|---|---|---|
|  |  |  |

T1, L1 = 2.6 um, 11 um
T2, L2 = 2.4 um, 9.1 um
T3, L3 = 3.8 um, 8.6 um
T4, L4 = 3.1 um, 8.3 um
Avg. Thickness = 3.0 um, Max. Length = 28 um
Aspect ratio = 28 / 3.0 = 9.3

T1, L1 = 1.7 um, 3.1 um
T2, L2 = 1.9 um, 26 um
T3, L3 = 1.8 um, 3.3 um
T4, L4 = 1.6 um, 3.8 um
T5, L5 = 1.6 um, 2.6 um
Avg. Thickness = 1.7 um , Max. Length = 35 um
Aspect ratio = 35 / 1.7 = 21

T1, L1 = 2.0 um, 4.3 um
T2, L2 = 2.3 um, 7.4 um
T3, L3 = 1.7 um, 4.3 um
Avg. Thickness = 2.0 um , Max. Length = 12 um
Aspect ratio = 12 / 2 = 6

Panel B
*sheets*

FIG. 5 (cont'd)

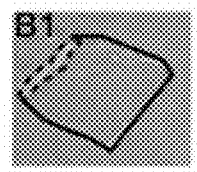 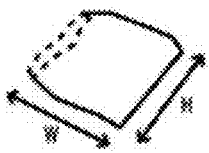

Small square plate, 19 um (W) x 18 um (H), with one visibly embedded ridge or fiber/tube on the shorter H axis of the plate. The fiber/tube (~ 2 um thickness/diameter) appears to cleanly terminate at the plate edge.

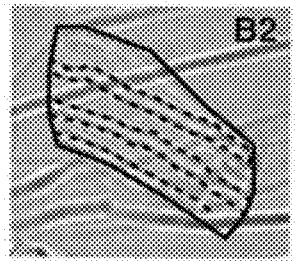 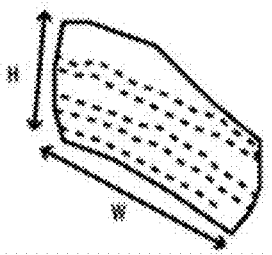

Medium irregular plate, 34 um (W) x 20 um (H), with three embedded ridges or fibers/tubes running parallel to the longer W axis of the plate. All three fibers/tubes appear to cleanly terminate at the plate edge.

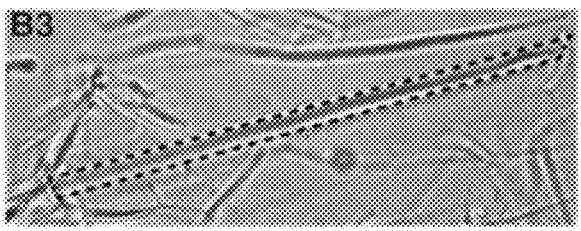

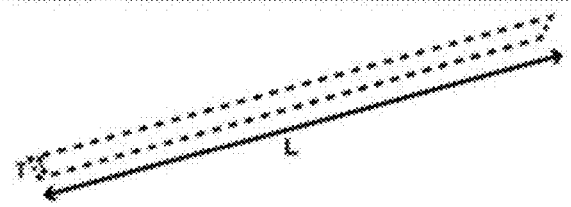

One long ridge or fiber/tube, with dimensions of 88 um (L) and 3 um (T) embedded in a large irregular plate with poorly defined edges.

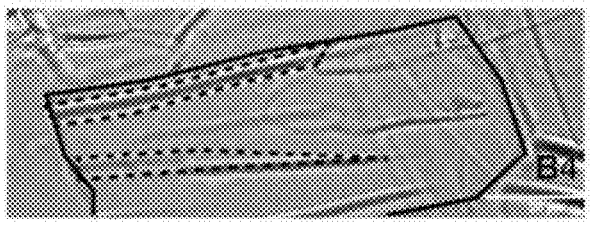

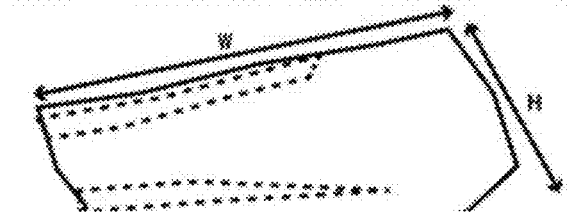

One large plate, 70 um (W) x 31 um (H), with at least two visible fibers/tubes running parallel to the longer W axis of the plate. The fibers/tubes appear to cleanly terminate at the plate edge.

FIG. 6A

Hardness

Very Soft — Lard (1) — Butter (2) — Shortening (3) — Coconut Oil (4) — Tallow (5) — Very Hard

Lubricity

Not lubricating (1) — (2) — Tallow (3) — Lard — Shortening (4) — Coconut Oil, Butter (5) — Very lubricating

Smoothness

Gritty (1) — (2) — Lard (3) — Tallow (4) — Butter, Shortening, Coconut Oil (5) — Smooth

Adhesiveness

Non-adhesive — Coconut Oil, Butter (1) — Lard, Shortening (2) — Tallow (3) — (4) — (5) — Very sticky Bacon model system (cooked)  Bacon model system (raw)

OLEOGEL HAVING A PROTEIN MICROSTRUCTURE WITH OPTIMIZED OIL RELEASE PROPERTIES FOR REPLACING STRUCTURED FATS AND SATURATED OILS IN FOOD AND COSMETIC PRODUCTS

FIELD OF THE INVENTION

This patent disclosure relates generally to climate change mitigation by using plant-based ingredients to replace animal derived fats and oils. Oleogel compositions with superior performance characteristics are provided for use in food and personal care products.

BACKGROUND

Food security—the reliable access to safe, affordable, and nutritious food—is inextricably linked to a predictable climate and to healthy ecosystems. Extreme weather, droughts, fire, and disease that result from climate change are already threatening the production of food around the world. Unless we act decisively, these problems will worsen, and the poorest and most vulnerable members of the world community will suffer disproportionately.

According to the United Nations Foundation in 2021, the worldwide yield growth for wheat, maize, and other crops has been declining for years, due to extreme heat and droughts. By some estimates, unless climate is reversed, global yields of agricultural products could decline by as much as 30% by 2050. Despite decades of efforts to improve the global food supply, widespread hunger persists at staggering rates. According to a 2019 report, nearly 750 million people worldwide experience undernourishment or food insecurity—and the numbers continue to rise.

Farm animals are high energy consumers, and they produce huge volumes of greenhouse gasses, contributing to climate change. Use in foods of solid tropical oils (such as coconut and palm oil) also has an adverse environmental impact by causing tropical deforestation, which compromises biodiversity.

The impact of society on the environment can be mitigated in part by decreasing the world's reliance on animal derived fats and tropical oils in the manufacture of foods and other products. Innovators in the food industry are placing an emphasis on developing plant-based foods that mimic traditional foods such as meat, fish, eggs, and dairy products. In a similar fashion, the beautification industry is taking steps to reduce the content of animal derived ingredients in cosmetics.

Texture, flavor, and mouthfeel of meat and dairy substitutes, and the moisturizing and beautifying effects of cosmetics, are all partly a function of the fats they contain. The fat and oil replacements provided in this disclosure can help develop more climate friendly foods and personal care products.

SUMMARY

This disclosure provides a protein oleogel with a protein dispersed in and providing structure to a liquid oil phase. The oleogel has a unique stability and functionality. It is designed, developed, and configured for use as a replacement for oil or structured fat in food, food ingredients, cosmetics, and personal care products.

The oleogel can be manufactured by a process that includes denaturing the protein in water, flash freezing and drying the protein, and then gradually adding a suitable oil or oil mixture. It has a microstructure in the form of fibrils, sheets, or other particles with substantial size in one or two dimensions, but that are not interconnected, and therefore free-flowing. The microstructure physically traps and structures the oil in which it is suspended. This provides for solid, free standing, fat-like performance, whereby the oil is released under shear or upon heating—much like traditional animal-derived structured fat.

As illustrated below, the oleogel has superior performance in food systems and in beauty care products. It releases oil upon cooking and chewing, thereby providing juiciness expected for fat-containing foods. The oleogel is spreadable, and forms an emulsion in aqueous liquid that is stable for at least six weeks without evidence of creaming.

Further aspects of the protein oleogel of this disclosure, its manufacture and use are put forth in the sections that follow.

Terms, Ranges, and Patent Terminology for Oleogel Compositions

The term "oleogel" as used in this disclosure has its ordinary meaning. It generally refers to a semisolid or solid-like material that is formed by a solid network of self-assembled molecules or oleogelators such as proteins or other polymers, which are able to immobilize liquid oil in within their structure, resulting in a semisolid or gel-like consistency. A semisolid has a pliable viscous consistency that is spreadable but does not pour in a narrow stream. The network provides the structural stability to the liquid oil phase, allowing it to maintain its form and texture at room temperature. When cooked, the network typically remains in place such that the oleogel softens and/or release a proportion of the oil contained therein. A protein oleogel may be characterized as a structured protein dispersed, distributed in, or encompassing a liquid oil phase, or as a composition or colloidal system where an oil or oil mixture is dispersed within and/or structured by the protein. These descriptions have similar meanings and (depending on context) are generally interchangeable.

The oil-protein compositions of this disclosure can be characterized or defined either: (1) according to the microstructure of the protein contained therein; (2) according to the method of manufacture; or (3) according to the performance properties of the composition once prepared. It can also be characterized by any two of these criteria: microstructure and manufacture, microstructure and performance, or microstructure and performance; or by all three criteria in combination. Similarly, the methods of this disclosure can be characterized or defined by the steps that are taken, and/or by the characteristics of the oleogel produced thereby, such as the microstructure of the oleogel and/or the performance of the oleogel, immediately after production and/or incorporated into a food or cosmetic product.

The term "protein oleogel" refers in this disclosure to a composition in which a protein is dispersed in a liquid oil phase, or an oil that is dispersed in and permeates a protein framework. The protein oleogels provided in this disclosure often have a total protein or oleogelator protein to oil ratio of at least 2:98 by weight, up to 40:60 by weight. More typically, they have protein to oil ratios of 2% to 40% up to 20% to 80%, 5% to 95% up to 15% to 85%; or an average of 5% to 95% by weight. The oleogel may be characterized as a protein oleogel of at least 30%, 50%, 70%, or 90% of the composition that is not oil is protein, and/or if the oleogel has been manufactured using a protein isolate as a primary ingredient.

The oleogelator protein that gives the oleogel its structure is typically but not necessarily a protein mixture or isolate. Alternatively or in addition, the protein used to structure the oleogel may be a single or multiple protein made by recombinant expression. Suitable mixed isolates are those that contain a median protein mol. wt. between 5 and 75 kDa, or about 10 to 50 kDa, optionally with an acidic isoelectric point (pH≤5). Exemplary is a protein isolate from potatoes, comprising patatins and/or protease inhibitors, such as the Solanic®200 or Solanic®300 fractions made by Avebe (Veendam, the Netherlands). See WO 2018/183770.

The oil can be any oil or oil mixture that is liquid at room temperature or upon heating. It may comprise fatty acids or other fatty structures in unsaturated or saturated form. Examples are provided in a later section of this disclosure. The oleogel composition may include other solid components or solutes such as crystallizable carbohydrates, maltodextrins, or polysaccharide derivatives that contribute to the oleogel, for example, by helping to form or stabilize the protein microstructure. The composition is typically produced and/or stored in a form that is substantially free of water or aqueous solvent: that is, less than 3% (wt/wt), preferably less than 1%. It may then be combined with aqueous solvents, oils, solids, other components, and combinations thereof for the purpose of analysis or in the course of manufacturing an industrial product therefrom.

The protein in the oleogel is often but not necessarily a plant protein. Alternatively or in addition, the protein may be an animal derived protein, or a protein that is produced naturally by microorganisms. The protein is typically denatured. This means that the protein no longer has its quaternary structure, tertiary structure, and/or secondary structure which is present in their native state. As a consequence, the protein generally loses enzymatic activity or other innate function. Denaturation may be achieved by application of some external stress or compound, such as a strong acid or base, a concentrated inorganic salt, an organic solvent such as alcohol, agitation, radiation, heat, or a combination thereof. The protein in the oleogel may be denatured during isolation from a plant before manufacture of the oleogel, and/or during the course of the oleogel manufacturing process (for example, by decreasing the pH and heating the solubilized protein isolate). Denatured proteins tend to be less soluble in aqueous solvents, increasing their tendency to form a stable microstructure in an oleogel.

At least some of the protein in the oleogel creates or exists as a microstructure that tends to reduce viscosity and/or increase hardness of the oil at room temperature. At least 10%, 30%, 50%, 70%, or 90% of the protein content in the oleogel (wt/wt) may be part of the microstructure. The contents of the microstructure that is protein (wt/wt) is at least 30%, 50%, 70%, or 90% protein, with most of the rest typically being other components of the protein isolate used to manufacture the oleogel.

The microstructure has dimensions and properties that imbue the oleogel with beneficial oil holding and releasing features described below and in the sections that follow. For example, the oleogel has a solid but pliable or a spreadable texture at room temperature. It retains the oil when stored at 4° C. or at room temperature. The term "spreadable" means that it can be spread freely and fairly evenly on an ordinary slice of bread using an ordinary butter knife at room temperature without inordinate effort, and without substantially deforming the bread slice. The oleogel fluidizers gradually upon heating, and/or releases some but not all of the oil upon cooking (typically between 20% or 30% and 60% or 70%). This contrasts with saturated and hydrogenated fats, which are solid at room temperature but melt quickly once heated to a transition point.

The oil retaining ability of an oleogel at different temperatures can be assessed by determining a melt curve, as illustrated in FIG. 4. Depending on its intended use, the melt curve of the oleogel has a descending slope that is not as steep as the slope for coconut oil. The oleogel melt curve may demonstrate that the oleogel retains some but not all of the oil when heated to typical cooking temperatures (for example, 160 to 200° C.; or 300 to 425° F.), indicated by a curve that bottoms out or continues only a gradual downward slope at these temperatures. The remaining oil may be between 20 to 80%, 10 or 30 to 60%, 25% to 75%, or 40 to 80% of the oil in the oleogel composition before heating.

Typically, the microstructure comprises particles that are at least 5, 10, or 20 μm in size in one or two dimensions or in all three dimensions. The particles are substantially not interconnected or intertwined. This means that pieces of microstructure that are more than 50 or 200 μm in any dimension are rare, comprising less than 10% or 2% of the microstructure by weight. In this configuration, the particles can pass by and between each other freely. The oleogel (including its suspended microstructure) will be free flowing if sufficiently diluted. The nature and shape of the microstructure and its component particles can be assessed by diluting the oleogel by 5, 10, 20, 50, or 100-fold vegetable oil, for example, using the dilution protocol provided later in this disclosure, and then observing the microstructure by light microscopy, scanning electron microscopy, or another appropriate visualization technology.

For example, the microstructure many contain fibrils having a median size that is at least 10, or 30 μm in length, typically at least 0.5 μm but less than 2, 3, or 4 μm in diameter. The term "fibril" refers to any shape that is long and skinny: it may or may not be rod shaped, ribbon shaped, hollow, or fiber-like. The fibrils may be free standing, branched, and/or clustered or entangled to form aggregates. For branched structures, length is defined as the longest linear span of the structure in three dimensions.

Alternatively or in addition, the microstructure may contain sheets. The sheets may have a median size that are at least 10 or 20 μm in length and width, typically at least 0.2 or 0.5 but less than 2, 3, or 4 μm in thickness. They may be folded, ruffled, or compacted together. Alternatively or in addition, the microstructure may have particles of rounded, faceted, or indeterminate shape. Such particles may be derived from the protein isolate used to make the oleogel, they may be generated during manufacture of the oleogel, or they may be formed by grinding, sonicating, or otherwise dispersing a larger, less malleable, or more solid or interconnected microstructure initially produced during manufacturing. To provide desirable oil retention and release properties, the particles are often designed to flow past each other by having a high median aspect ratio (diagonal length to thickness) of at least 3, typically at least 5, 7, 10, or 15.

The oleogels having the composition described above, manufactured as described below, or having desirable properties put forth throughout this disclosure can be used in the preparation of food products or ingredients, or cosmetic or personal care products. This can reduce the dependency of such products on animal-derived fats and other renderings, thereby mitigating at least some of the effects of climate change.

Descriptive terms used as a guideline for proportional amounts of a component or preparation are as follows: "some" means at least 10% or 20%, "most" means more than 50%, "substantially all" means at least 90%, wherein the component(s) that constitute the remaining 10% or less do not substantially affect performance characteristics of the mixture or product. Proportional amounts are given in units of wt/wt, unless stated otherwise.

Particular embodiments, aspects, properties, and features of the oleogel of this disclosure, its manufacture and use are described and exemplified in the sections that follow.

Trademark

Oleogels having characteristics described herein and/or manufactured by a process put forth herein may be referred to in this disclosure and elsewhere under the name Oleo-Pro™, a trademark of Shiru Inc.

The images were obtained by diluting each of the two oleogel preparations 1 to 10 in vegetable oil. Both types of microstructure comprise particles that are at least 10 μm in one or two dimensions, but are substantially not interconnected and free flowing. This contributes to the oil structuring and retention properties that make these oleogels suitable as replacements for animal derived fats and oils.

Figure 1:
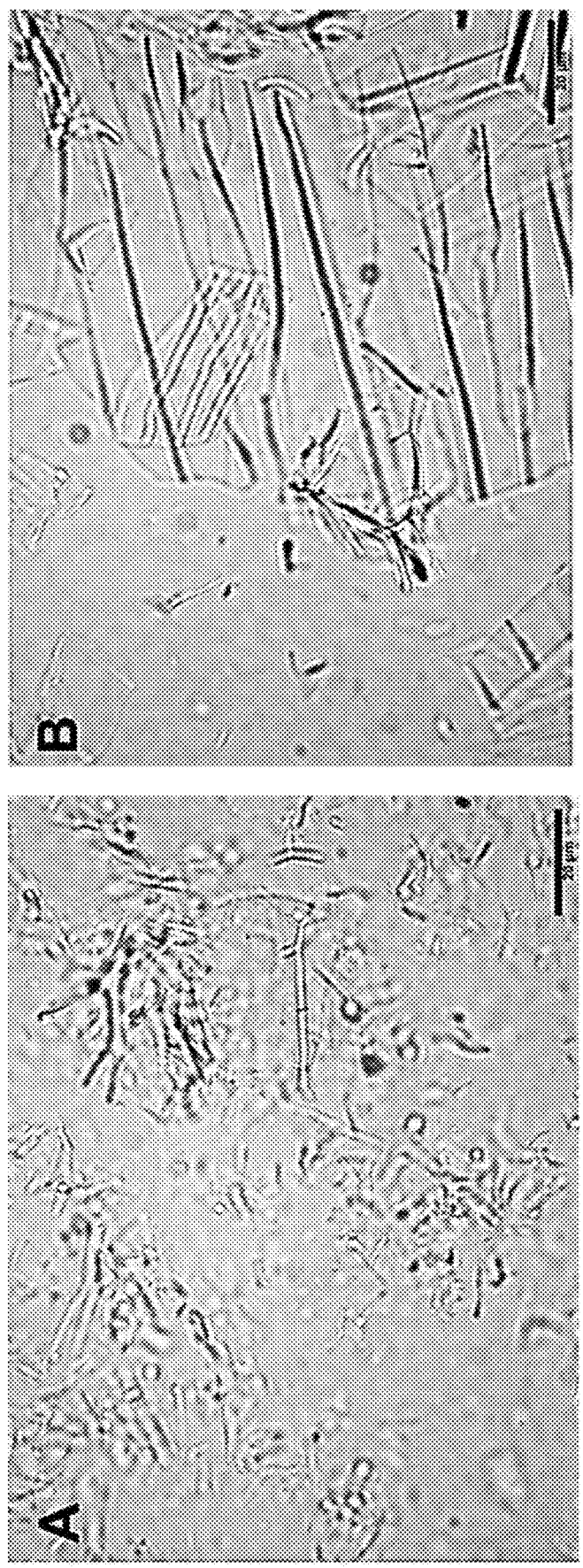
FIG. 1 shows light micrographs of two different oleogel preparation having plant protein microstructures in accordance with this disclosure. The scaling bar in the bottom of each panel represents 20 μm in length. Panel (A) shows a preparation that was made by flash freezing denatured plant protein in a 1% (wt/wt) solution, followed by drying and combining with high oleic acid sunflower seed oil. The field shows fibrils, branched fibrils, and fibril clusters or entanglements. Panel (B) shows another preparation made substantially the same way, except that the denatured protein solution was flash frozen at a concentration of 5% (wt/wt). This field comprises protein sheets. The upward sloping lines are folds in the sheets and embedded fibrils.
Figure 2:
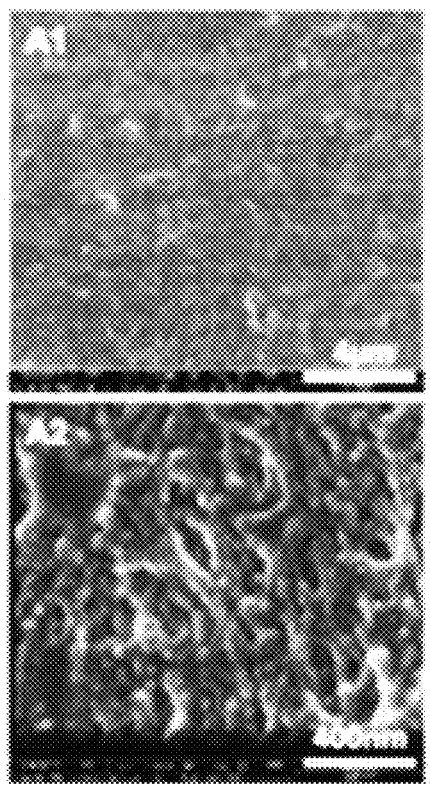
Figure 2:
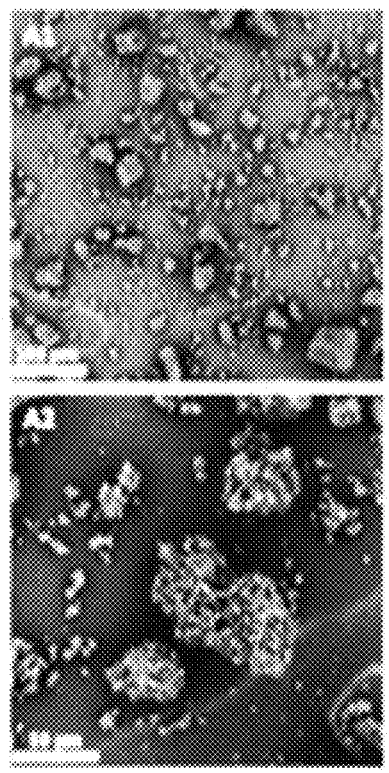
Figure 2:
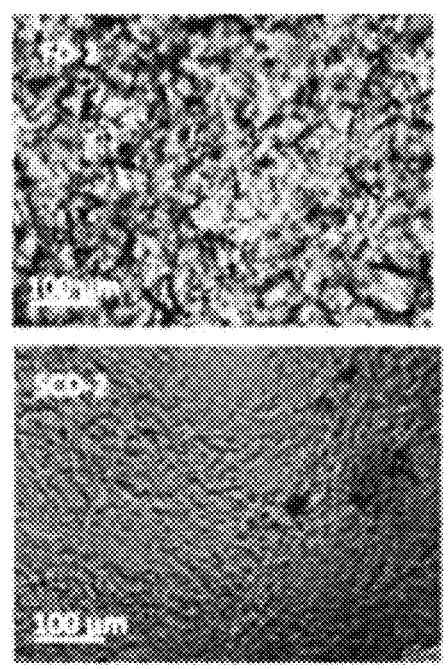
Figure 2:
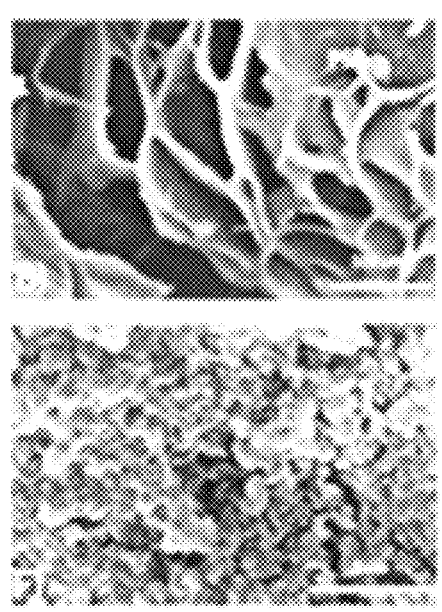
Figure 2:
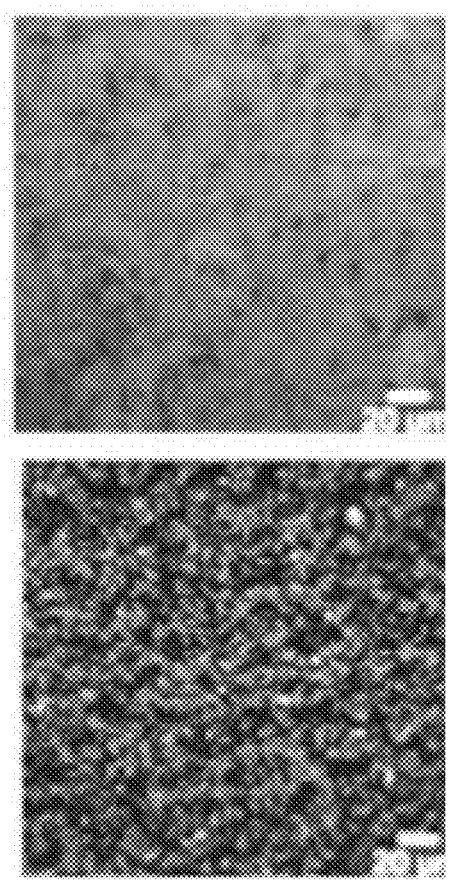
Figure 2:
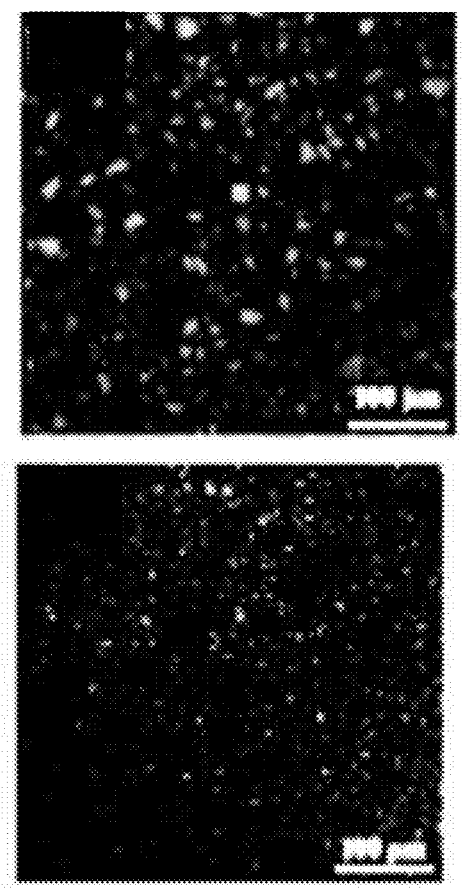

FIG. 2 is a consolidation of micrographs adapted from publications reporting previous protein oleogels. The images from refs (A), (C), (D) show mesh and honeycomb type microstructures. The images from refs. (B), (E), and (F) show pebble-like solids and microaggregates that are round or ellipsoid in shape or aggregates thereof, thereby having an aspect ratio (length to thickness) that is no more than two. None of the previous protein oleogels has anything like the fibrils and sheets shown in FIG. 1—and as a consequence, have inferior oil holding and release properties.

Figure 3A:
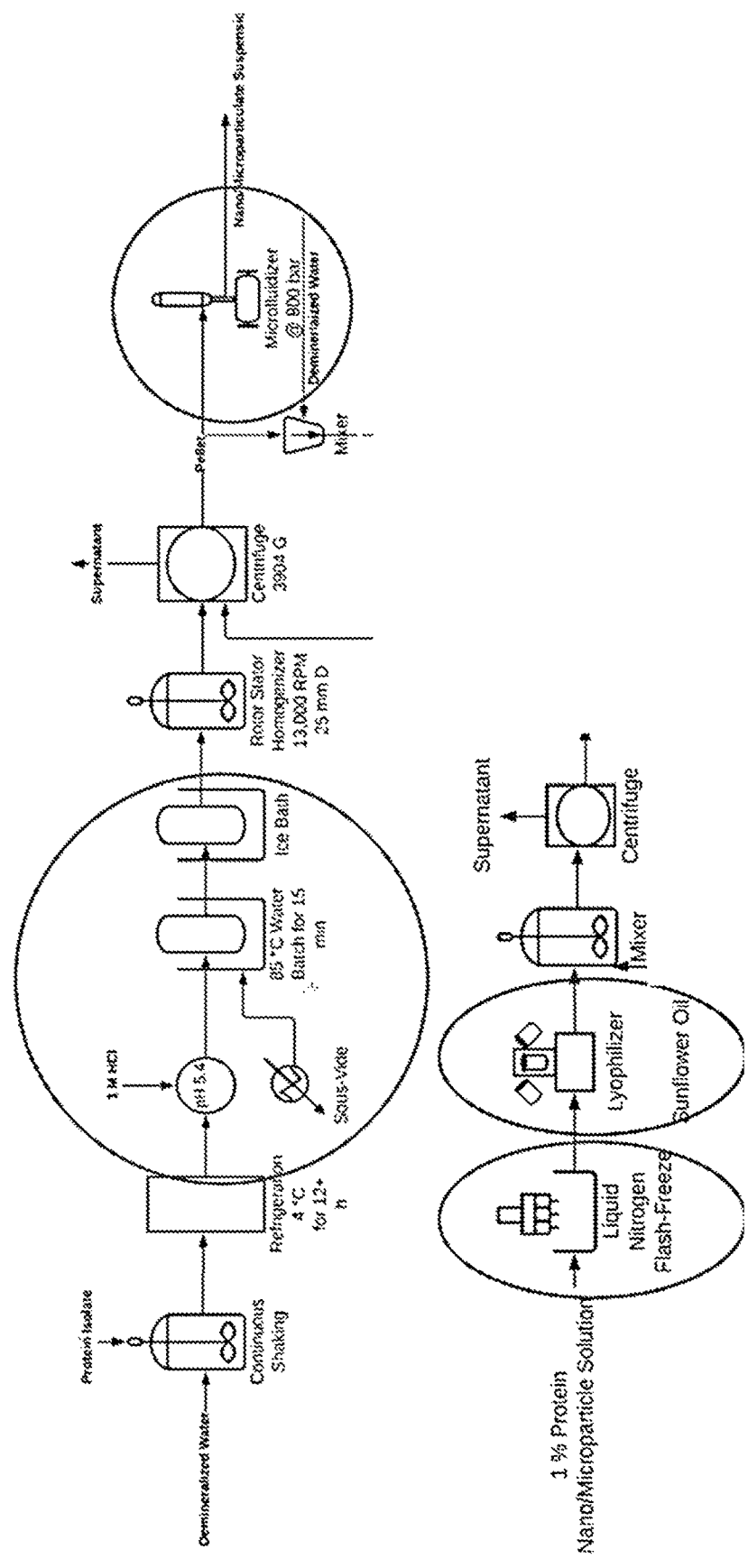
Figure 3B:
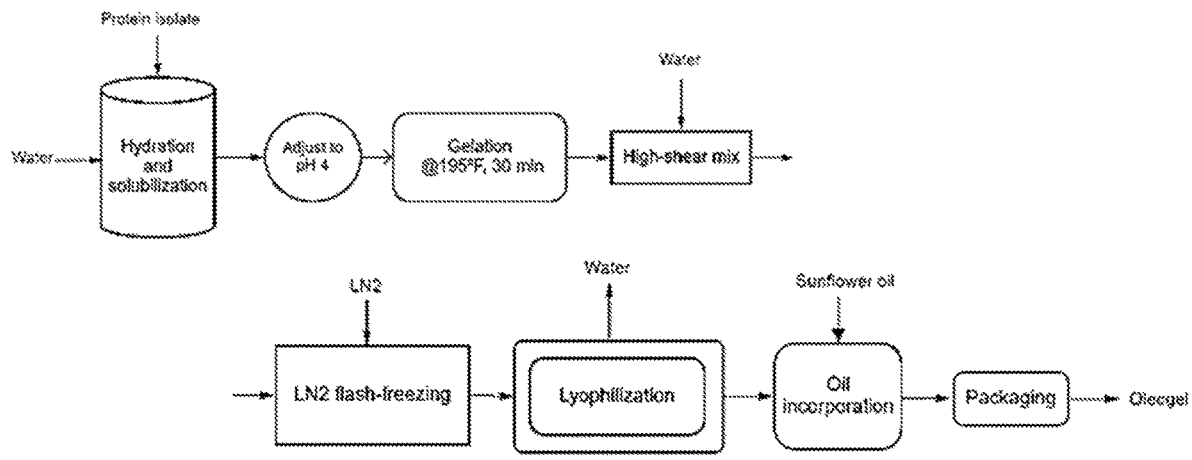

FIG. 3A is a flow chart that provides an overview of procedural steps that can be used for optimizing a manufacturing an oleogel according to this disclosure. FIG. 3B is a flow chart that illustrates one possible way of manufacturing an oleogel having the microstructure shown in FIG. 1. The starting protein isolate is hydrated and solubilized, and then acidified and heated to denature the protein. A clear stranded gel is formed. This is blended, flash frozen, and dried to form a powder. Oil is added to the prepared powder gradually to preserve the inherent microstructure and form the oleogel.

Figure 4:
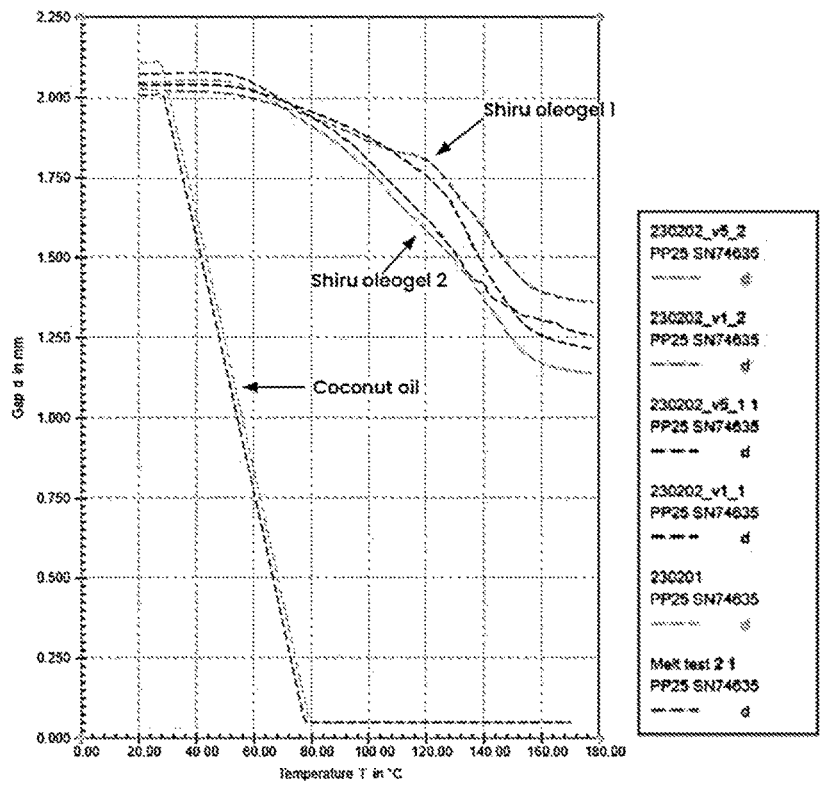

FIG. 4 is a melt curve that compares two determinations for each of two different protein oleogel preparations according to this disclosure with coconut oil. Curves obtained for several oleogel preparations are gently downward sloping, showing gradual release of a substantial proportion of oil as they are heated to cooking temperatures. The curves do not descend all the way to zero, because not all of the oil is released. There was some residual oil in the protein structure after heating.

Figure 5:
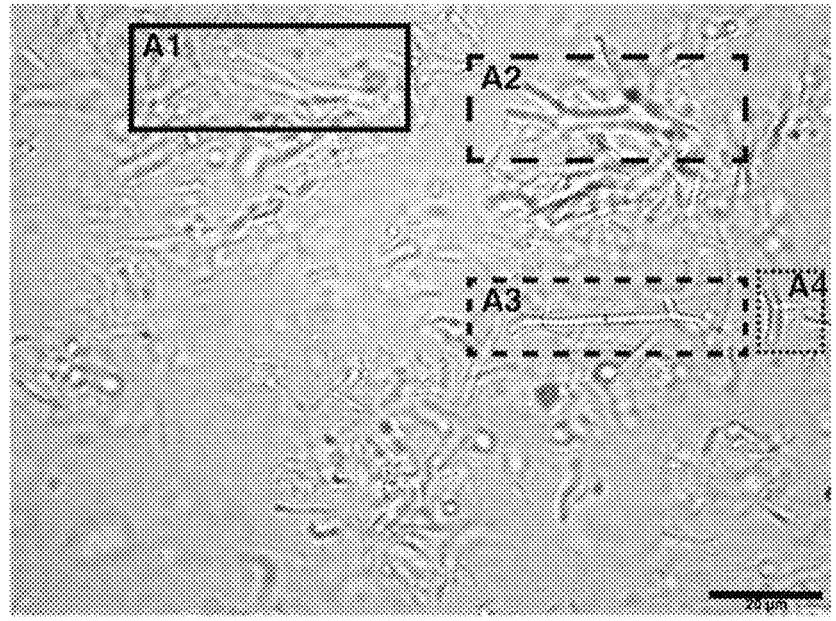
Figure 5:
Figure 5:
Figure 5:
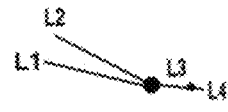
Figure 5:
Figure 5:
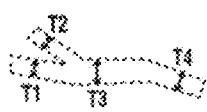
Figure 5:
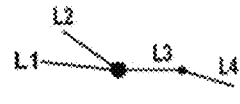
Figure 5:
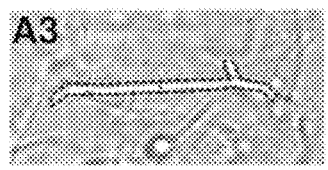
Figure 5:
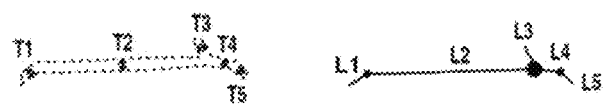
Figure 5:
Figure 5:
Figure 5:
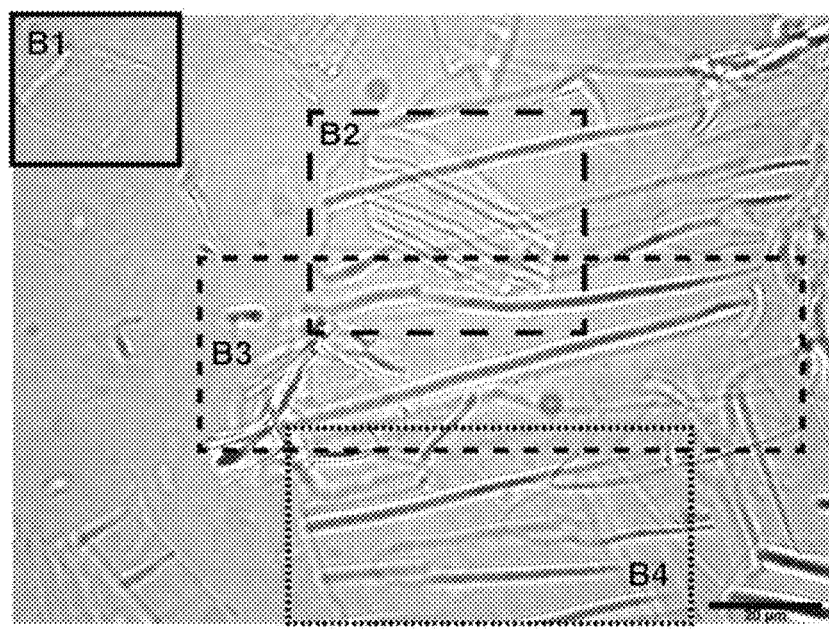

FIG. 5 is a quantitative analysis of the oleogel microstructures taken from FIG. 1. Details A1, A2, A3, and A4 are representative fibrils or ribbons that were measured by comparing the image details with the 20 μm scale bar. Total length from end to end (including branches) ranged from 12 to 35 μm. Diameter ranged from 1.7 to 3.0 μm. Aspect ratio (length to diameter) ranged from 9 to 21. Details B1, B2, B3, and B4 are representative plates of different shapes. Length or height ranges from 19 to 88 μm; width ranges from 18 to 42 μm. Given a thickness of 2 μm, the aspect ratio (length to thickness) ranged from 10 to 44.

Figure 6B:
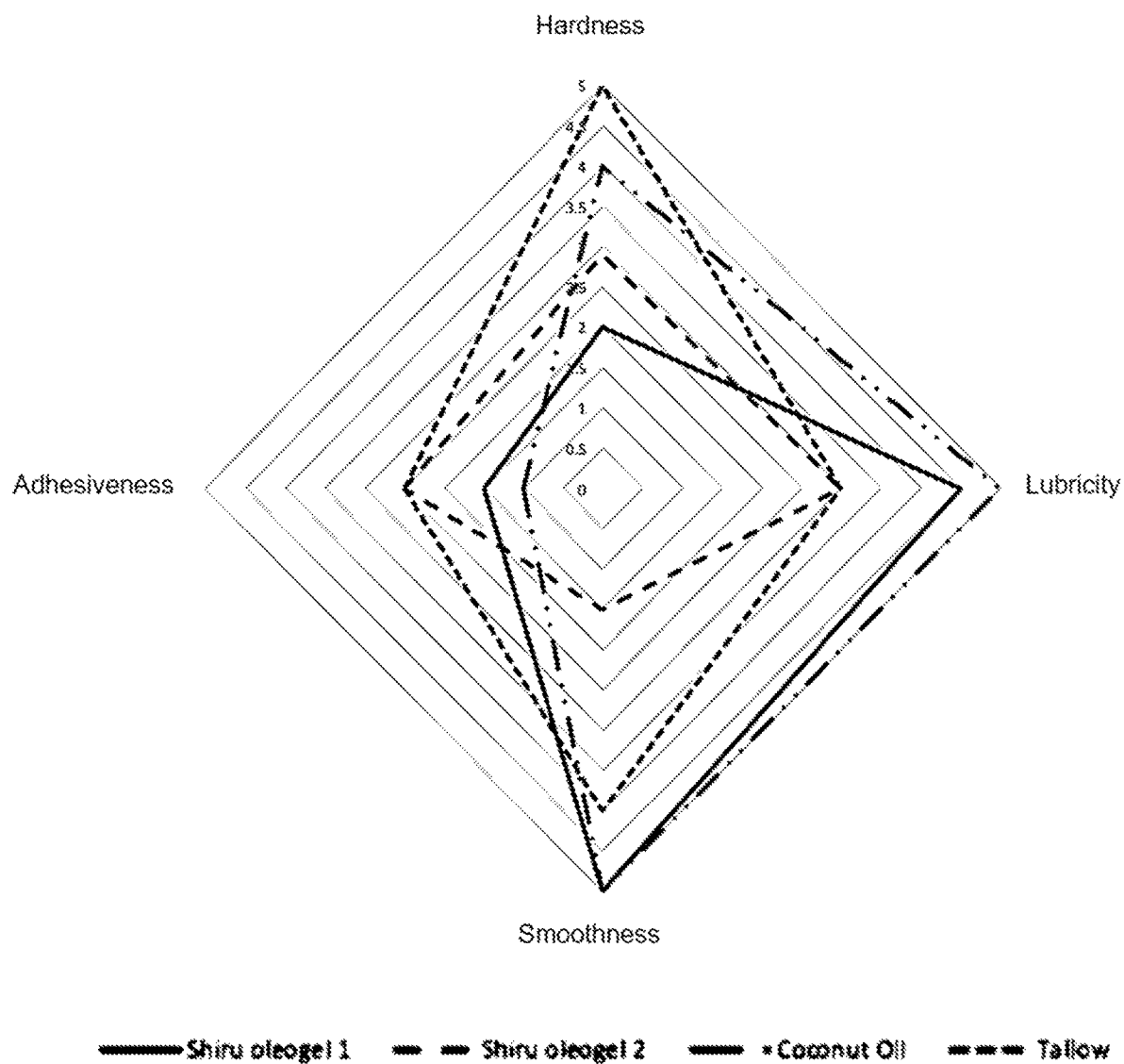

FIG. 6A shows the five-point scale for subjectively assessing gel characteristics. Protein oleogels prepared in the manner described scored as follows: Hardness=2, lubricity=4.5, smoothness=5, and adhesiveness=1. FIG. 6B presents the subjective data of these criteria as a spider plot. The solid line marked "Shim oleogel 1" was made by the manufacturing process outlined above. High values for lubricity and smoothness are prominent.

Figure 7:
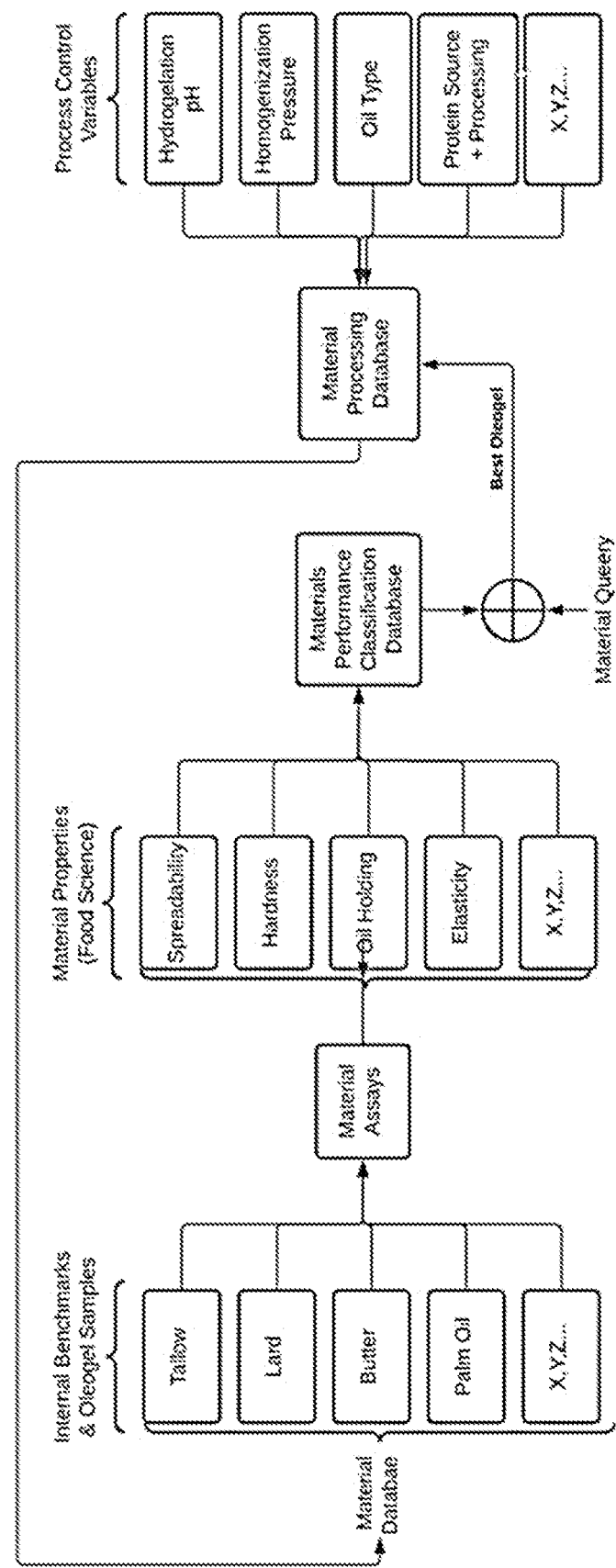

FIG. 7 is a flowchart suitable for iteratively and empirically optimizing process control variables (right column) by measuring sensory properties using internal benchmarks (left column) and material properties (middle column).

Figure 8A:
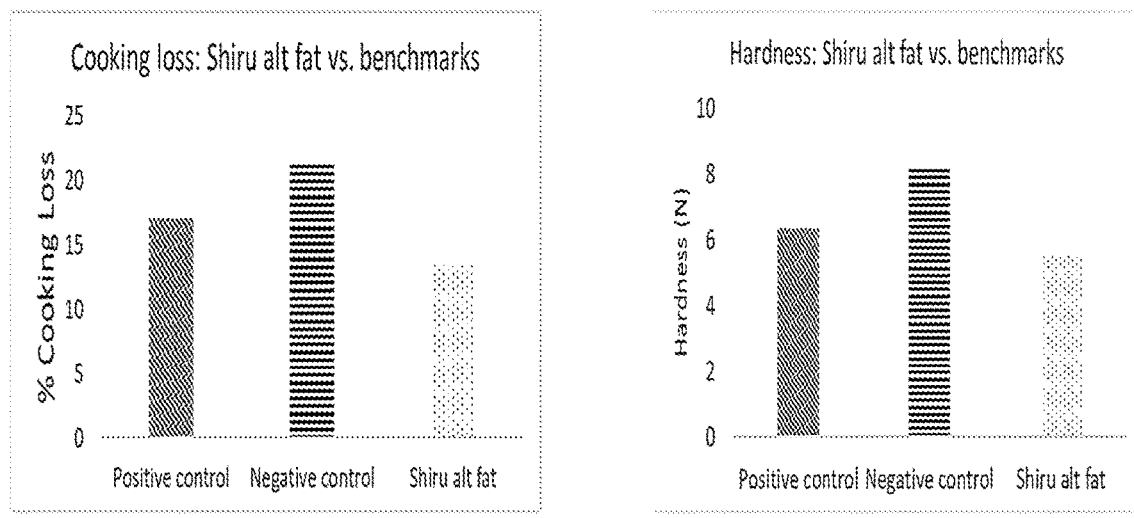
Figure 8B:
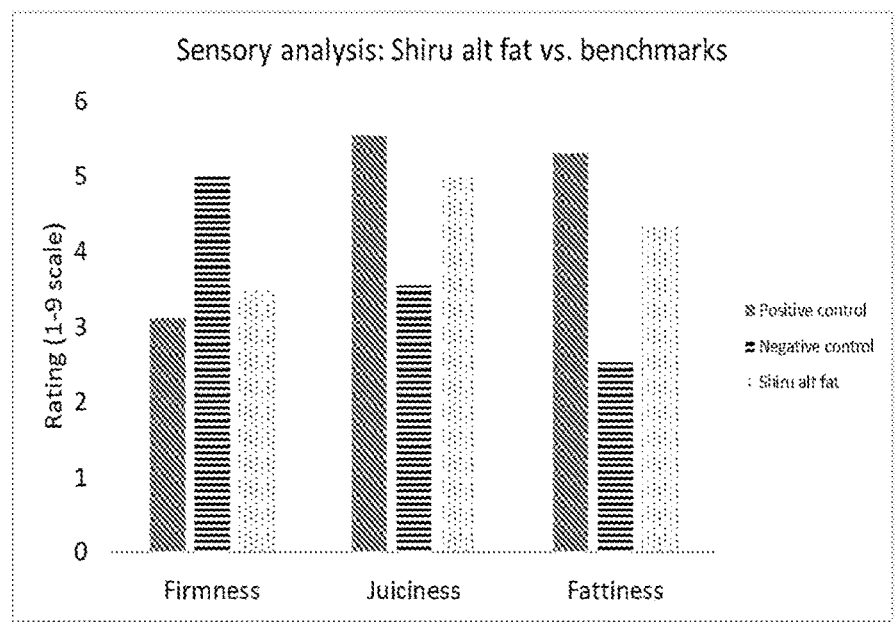

FIGS. 8A and 8B show features of burger patties made with protein oleogel. FIG. 8(A) shows weight loss during cooking and hardness measured mechanically. FIG. 8(B) shows perceived firmness, juiciness, and fattiness assessed by a panel of trained volunteers.

Figure 9:
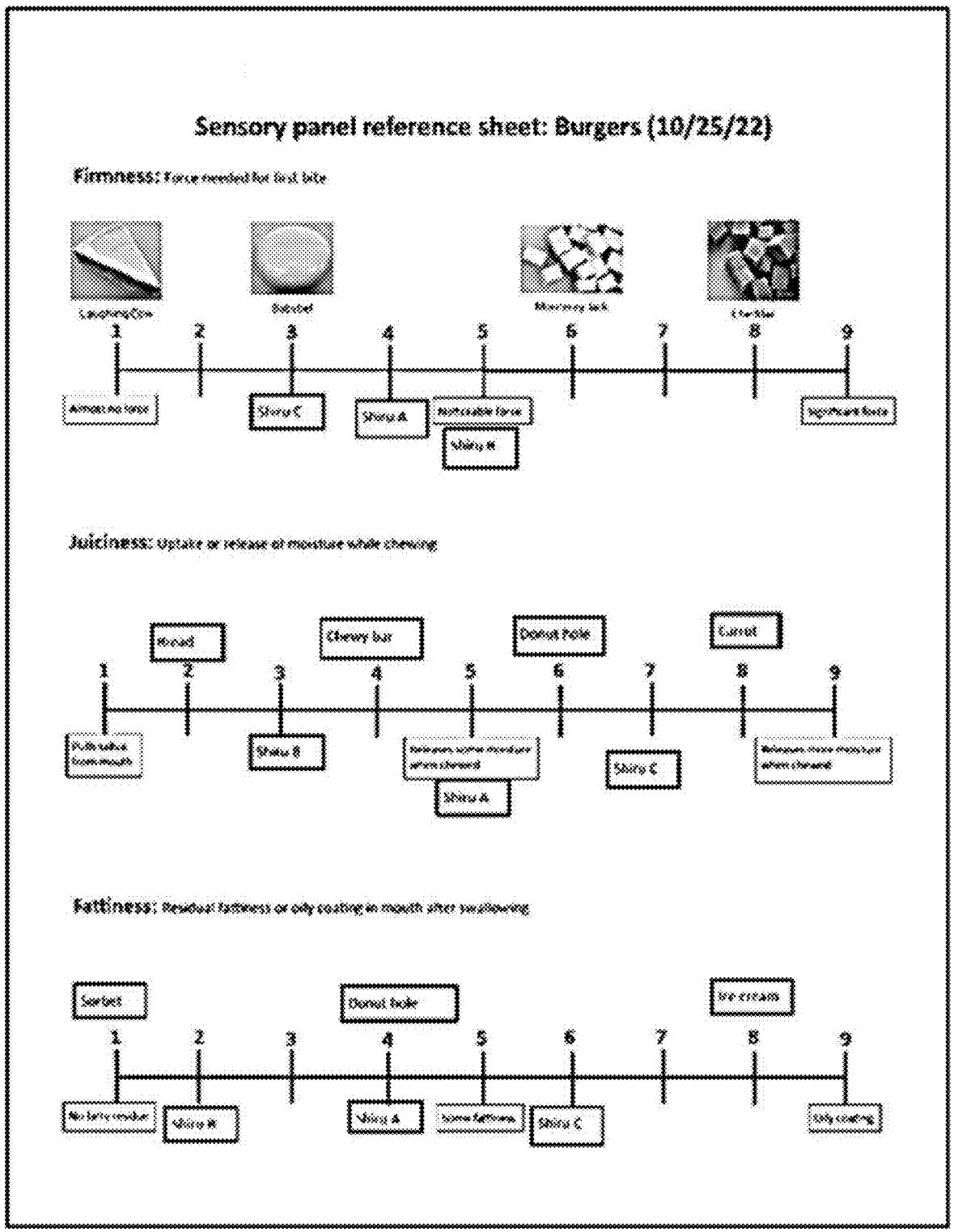

FIG. 9 is a scale used to evaluate the patties by sensory criteria.

Figure 10:

FIG. 10 shows the spreadable texture of a protein oleogel manufactured in accordance with this disclosure.

Figure 11:
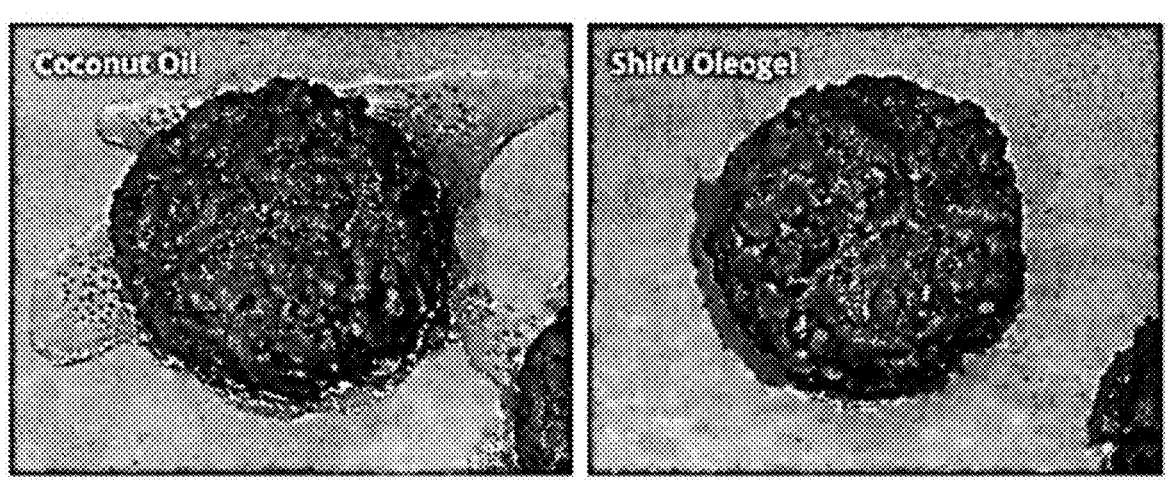

FIG. 11 provides two photographic images comparing test patties made with coconut oil or with protein oleogel when heated to cooking temperature. Oil oozed and bubbled away from the patty made with coconut oil, but not from the patty made with protein oleogel.

Figure 12:

FIG. 12 shows protein oleogel according to this disclosure that is incorporated as discrete pockets into a plant-based replacement product for bacon.

DETAILED DESCRIPTION

Described in the following sections are oleogel compositions having a protein microstructure. The oleogel can be used in a variety of applications, including food, personal care, and pharmaceuticals. The oleogel is stable and has excellent mechanical properties, making it ideal for use in products that require a semisolid or a solid but meltable consistency. The oleogels are capable of large-scale manufacturing, and have superior properties for inclusion in processed foods, cosmetics, and personal care products.

Interrelationship Between Oleogel Microstructure, Method of Manufacture, and Functional Properties The protein oleogels of this disclosure can be characterized in terms of any one of three types of features put forth below—either alone, or in combination with one or both of the other features. (1) The protein microstructure of the oleogel; (2) the method of preparation or manufacture of the oleogel; and (3) oil release properties and physical and sensory characteristic of the oleogel after it is produced.

Although these features may be characterized separately, they are operationally interrelated. The properties of the oleogels of this disclosure are a function of or influenced by the microstructure of the oleogel, which in turn is a function of or influenced by the methodology used to manufacture the oleogel. The oleogels, their features, their preparation and use are elaborated in the sections that follow.

Previous Oleogels and their Use

An organogel is a class of gel composed of a liquid organic phase within a structured network. An oleogel is an organogel with an oil as the organic phase. Oleogels are lipophilic liquid and solid mixtures, in which solid lipid materials (oleogelators) (<10 wt %) entraps and solidifies bulk liquid oil (typically a mixture of edible fatty acids) by ways of the network of oleogelators in the bulk oil.

A commonly used structurant for oleogels is ethyl cellulose: a polysaccharide manufactured from wood pulp. It is a semi crystalline derivative of cellulose that can be introduced into edible oils by direct dispersion. Its gel forming ability is attributed to its hydrophobic nature and semicrystalline characteristics. To induce gelation, ethyl cellulose is heated to 130° C. (beyond its glass transition temperature). Subsequent cooling forms rigid intermolecular interactions linked by hydrogen bonds, creating a three-dimensional entangled network from one-dimensional polymer strands that is responsible for entrapment of oil. F. Manzoor et al., Food Hydrocolloids for Health, Vol 2: December 2022.

E.I. Du Pont De Nemours and Company appetizingly describes ethyl cellulose this way: Ethocel™ polymers are water-insoluble thermoplastic polymers; they can therefore be employed for a wide variety of functions. They are used for rheology modification, film formation, binding, water barriers, and as time-release agents. Ethocel™ can also be effectively used as a sacrificial binder as they exhibit clean burn out.

Oleogels are internally structured, and can be used to replace structured oils commonly used in processed foods, particularly animal fats. The field of oleogel research has been active in recent years, generating products with desirable properties like thermal resistance, texture, and structural stability. Depending on the matrix underlying the oleogel, food products have been shown to resemble textural attributes of products conventionally made with conventional hardstock fat, to affect nutritional qualities, to demonstrate high physical and oxidative stability, and to exhibit a high oil binding capacity.

An excellent review article by C. Park and F. Maleky (Front. Sustain. Food Syst. 4:139, 2020) provides an overview of oleogels that have been incorporated into various types of food products. Such food products are shown below in TABLE 1. The reader is referred to the Park article for the cited publications that describe the products listed in the table and the types of oleogels they incorporate.

TABLE 1

Examples of oleogel applications in food product formulation.

| Food products | Liquid oil type | Organogelator type |
| --- | --- | --- |
| MEAT PRODUCTS | | |
| Frankfurter | Soybean; canola; sunflower | Rice bran wax; ethylcellulose γ-oryzanol and phytosterol |
| Meat patties | Linseed; sesame | Oryzanol and β-sitosterol; beeswax |
| DAIRY PRODUCTS | | |
| Cream cheese and processed cheese products | High oleic soybean; soybean; | Rice bran wax; ethycellulose and sunflower wax |
| Ice cream | High oleic sunflower; sunflower | Rice bran wax: γ-oryzanol and phytosterols |
| SPREADS | | |
| Margarine | Soybean | Sunflower wax, rice bran wax, and candelilia wax |
| Spread | Sunflower; virgin olive and hazelnut | Sheliac wax; beeswax and sunflower wax |
| CONFECTIONARIES | | |
| Chocolate paste | Sunflower; pomegranate seed and palm | Shellac wax; monoglyceride, beeswax, and propolis wax |
| Chocolate | Sunflower; hydrogenated palm kernel | γ-oryzanol and β-sitosterol ethycellulose |
| Filling | Rice bran and palm; canola | Beeswax; hydroxypropyl methylcellulose and methylcellulose |
| PASTRIES | | |
| Cookie | Refined hazelnut; canola; rice bran oil | Beeswax and sunflower wax; candelila wax; bleached rice bran wax |
| Cake | Sunflower; cotton and high oleic sunflower | Beeswax, candellila wax, and rice bran wax; carnauba wax. |
| OTHER APPLICATIONS | | |
| Oleogels as carriers of bioactive compounds | High oleic sunflower; canola | Beeswax with β-carotene; ethylcellulose with β-carotene |

None of the oleogels listed in TABLE 1 are made with protein as the oleogelator. The owners and inventors of the technology described in this disclosure have developed protein oleogels that have superior properties to replace animal fats and other components in food and cosmetic products.

Unique Microstructure of the Oleogels of this Disclosure

An oleogel according to this disclosure can be characterized as having a microstructure with certain observable features.

FIG. 1 is a pair of light micrographs of an oleogel preparation produced by optimized freeze channeling, drying, and oil dispersion. The scaling bar in the bottom of each panel is 20 µm in length. Panel (A) shows a preparation that has been diluted to 1% in oil. The field shows fibrils and fibril clusters or entanglements. The fibrils are 30 to 50 µm in length and 1 to 3 µm in diameter. The fibrils may be solid (rod-like) or hollow tubes with varying degrees of branching. Individual branches or unbranched structures are commonly 10-50 um in length.

In addition to the fibrils, microstructures in the form of tetragonal or irregular sheets can also be observed. Panel (B) shows a preparation that has been diluted to 1% in oil following flash-freezing and freeze-drying of a 5% w/v protein solution. Representative sheet structures exhibit a wide range of estimated planar dimensions, on the order of 10 µm×10 µm (length×width) to greater than 10 µm×100 µm. The sheets may be less than 2 µm, 1 µm, or 0.5 µm thick. Often, as shown in Panel (B), the sheets appear as ruffled or textured with embedded ridge-like features.

Typically, the microstructure represents greater than 50% of oleogelator protein or total protein in the composition. Water insoluble microstructures typically comprise ~50% of the freeze-dried protein material before the oil is added. This can be determined by dispersing the processed protein powder in water, centrifuging at 14×g at 24° C. for 30 min, and measuring the soluble protein content in the supernatant using the bicinchoninic acid assay (Thermo Fisher Scientific). The protein in the composition is predominantly associated with the microstructure when dispersed in oil. Differences Between the Microstructure Shown Here and the Microstructure of Previous Protein Oleogels The oleogel microstructure shown here is new for protein oleogels: it differs considerably from microstructures observed in oleogels previously made using protein as the oleogelator.

FIG. 2 is a consolidation of optical images, confocal micrographs, and SEM micrographs adapted from the following prior publications:

(A) *Protein oleogels from protein hydrogels via a stepwise solvent exchange route*. Auke de Vries et al., Langmuir. 2015 Dec. 29; 31(51):13850-9.

(B) *Controlling agglomeration of protein aggregates for structure formation in liquid oil*: A Sticky Business. Auke de Vries et al., ACS Appl. Mater. Interfaces 2017, 9, 11, 10136-10147.

(C) *Structural characterization of oleogels from whey protein aerogel particles*. S. Plazzotta et al., Food Res Int. 2020 June; 132:109099.

(D) *Structural characterisation and absorption capability of whey protein aerogels obtained by freeze-drying or supercritical drying*. L. Manzocco et al., Food Hydrocolloids, Vol 122, January 2022, 107117.

(E) *Protein oleogels prepared by solvent transfer method with varying protein sources*. A. Feichtinger, E. Scholten et al., Food Hydrocolloids, Vol 132, November 2022, 107821.

(F) *Formation of protein oleogels via capillary attraction of engineered protein particles*. S.-S. Wang et al., Food Hydrocolloids, Vol 133, December 2022, 107912

The images in FIG. 2 are described in the aforelisted references as follows:

(A) SEM micrographs of whey protein isolate (WPI) at two different magnifications.
(B) SEM micrographs of WPI particles shown at two different magnifications.
(C) Optical micrographs of a freeze-dry WPI aggregate (upper panel), contrasted with aggregates produced using super-critical drying (lower panel).
(D) SEM micrographs showing continuous WPI aerogel produced by freeze-drying (upper panel) or supercritical drying (lower panel).
(E) Confocal microscopy of WPI of aqueous microgel pellets (upper panel) and corresponding oleogel (lower panel) made with WPI.
(F) Confocal laser scanning microscopy (CLSM) of protein aggregates after homogenization by a stator-rotor dispenser (upper panel) or ball milling (lower panel).

TABLE 2 compares each of the references (Col. 1) on the basis of oil structuring mechanism, the starting protein, the colloidal form of the protein after heating, and the morphology of the respective microstructure observed in oil (Col. 5).

TABLE 2

Microstructure of previously published protein oleogels

| Ref. | Oil structuring mechanism | Initial protein input | Colloidal form of the protein | Microstructure morphology (in oil) |
|---|---|---|---|---|
| (A) | hydrogel solvent exchange | WPI (Whey protein isolate) | fine-stranded or aggregate hydrogel mesh network | "mesh": smooth (<100 nm) to course mesh structure of original hydrogel |
| (B) | direct dispersion of structured freeze-dried particles | WPI | ~150 nm heat-set protein aggregate/microgel particles | pseudo-spherical "pebbles": (~50-100 um) porous agglomerates for freeze-dry procedure |
| (C) | direct dispersion of structured freeze-dried/supercritical $CO_2$-dried particles | WPI | heat-set protein microgel particles | "mesh": 300-700 nm porous aerogel particles (dying method dependent) |
| (D) | direct dispersion of structured freeze-dried/supercritical $CO_2$-dried particles | WPI | hydrogel mesh network | "mesh": porous aerogel scaffold |
| (E) | direct dispersion of structured, solvent dried particles | WPI (Whey), EPI (Egg), PPI (Pea), SPI (Soy), Solanic® 200 PoPI (Potato) | ~100 nm-10 um heat-set protein microgels/aggregates (protein dependent) | pseudo-spherical "pebbles" (assumed spherical for sizing w/ Mie Theory) |

TABLE 2-continued

Microstructure of previously published protein oleogels

| Ref. | Oil structuring mechanism | Initial protein input | Colloidal form of the protein | Microstructure morphology (in oil) |
|---|---|---|---|---|
| (F) | ball-mill dispersion of protein particles and water | WPI, Tannic-Acid treated zein (hydrophilic treatment) | aggregates prepared by ~200 nm spherical zein "bottom-up liquid-liquid dispersion (anti-solvent precipitation)"; ~150 nm heat-set WPI aggregates (de Vries et al. 2017) | spherical aggregates, capillary bridged with water |

As is evident in FIG. 2, the mesh type microstructures (A), (C), and (D) and the pebble type microstructures (B), (E), and (F) of previous perspirations are unlike the fibrils and sheets for the oleogels of this disclosure shown in FIG. 1. Not to imply any limitation on the invention described and claimed herein, the makers of this invention suppose that differences in the preparation account for the differences in the protein microstructure. The oleogels of this disclosure benefit from optimized freeze channeling, drying, and oil dispersion. For example, in ref (A), water is removed by solvent exchange to avoid agglomeration. Too much agglomeration may generate microstructures that are continuously interconnected as a solid mass, or in a rigid honeycomb shape.

The microstructure in turn is believed to affect the working properties of a microgel that contains it. Not to imply any limitation on the invention described and claimed in this patent application, oleogels having an underlying pebble type microstructure tend to be semi soft at room temperature and melt completely upon heating. On the other hand, oleogels having an underlying microstructure in the form of a large solid mesh or honeycomb tend to be solid at room temperature, and remain solid on heating. The data presented in this disclosure demonstrates that the Goldilocks optimum is a microstructurant that consists mostly of fibrils, sheets, and similar structures that have a high aspect ratio: they are sizeable in one or two dimensions, but substantially flat without extensive interconnectedness Protein oleogels with these microstructures are pliably solid or of spreadable consistency at room temperature, and release some but not all of their oil content gradually during cooking. The melt curve for a protein oleogel with this type of microstructure is discussed in a later section of this disclosure.

A theoretical elaboration for the relationship of microstructure to functional properties is as follows. A high surface area provided by a high aspect ratio of microparticulated protein structures can seed fat crystal nucleation or otherwise contribute to the alignment of aliphatic chains of unsaturated fatty acids, thus increasing intermolecular forces in the oil and leading to semisolid materials properties. Oleogels produced by adding oil directly to the initial protein isolate without denaturing or drying produces a suspension with poor oil holding and non-standing (non-solid) structures. Besides size and shape of the microparticulated proteins and microgels, rigidity of the particles may influence the mouthfeel because of their tribological (frictional) properties.

Assay for Determining Oleogel Structure

Once a protein oleogel has been manufactured or otherwise obtained, the reader may characterize the microstructure using light microscopy, confocal microscopy, scanning electron microscopy (SEM), or other technique that visualizes microparticles in the micron range The light micrographs shown in FIG. 1 were obtained by preparing protein oleogel preparations as follows. Starting with a protein oleogel comprising a protein dispersed in a vegetable oil in liquid oil phase and substantially free of water: 0.1 grams of the oleogels mixed for 1 minute using a benchtop vortexer (Vortex® Genie 2) on its highest setting. The resulting suspension is directly imaged on a light microscope using an oil immersion 100× microscope objective.

To monitor or to optimize the manufacturing process, intermediates of the process can be analyzed n a similar fashion: for example, the starting protein isolate, the hydrogel formed by first dissolving the protein isolate in water, and the dry micro particulate powder obtained after freeze-drying the hydrogel. The micro particulate powder can be imaged as a dispersion in an aqueous phase, or in an oil/aqueous phase.

Overview of Manufacturing Process for Making Protein Oleogels

With few exceptions, protein isolate mixtures by themselves are sparingly soluble in water or aqueous solvents. Oleogels having protein as the oleogelator are usually made by a multi-step process.

Previously, some protein oleogels were made using an emulsion template approach, high internal phase Pickering emulsions (HIPE's) are formed whereby an emulsion is first prepared using protein as an emulsifier, followed by stripping off the aqueous phase. Alternatively, protein oleogels were made via solvent exchange. First, a hydrogel is prepared by dispersing the hydrophilic protein in water followed by heat treatment so that hydrophobic groups of globular proteins are exposed. This establishes hydrophobic interactions and results in strong physical and covalent interactions linking proteins via disulphide bridge formation. After the network has formed, water is removed in a stepwise manner using organic solvents with medium polarity to avoid any coalescence-induced disruption of the protein network. After completely replacing water with solvent, oil is induced into the system, resulting in an oleogel with less than 1% water. F. Manzoor et al., Food Hydrocolloids for Health, Vol 2: December 2022.

The owners and makers of this invention have developed a particular oleogel preparation strategy and methodology. The procedure when empirically optimized promotes formation of an effective oleogel microstructure, with beneficial properties ensuing therefrom. The following sequence of steps is recommended to the reader.

1. Hydrate and solubilize the starting protein isolate into purified water;
2. Make the dissolved protein moderately acidic (pH of 2 to 4);

3. Denature the protein with heat below boiling temp for a modest period of time (such as min), which may form a clear stranded gel;
4. Blend the denatured protein using a high shear mixer such as an immersion blender or overhead stirrer;
5. Flash freeze (for example, by spraying into liquid $N_2$);
6. Dry the frozen protein in a manner that doesn't disturb the emerging microstructure (for example, by lyophilization) to form a powder;
7. Add an oil gradually and gently to the prepared powder in a manner that maintains the aspect ratio of microstructure particles.

FIG. 3A is a flow chart that provides a scheme for evaluating and adjusting aspects of this procedure. With the objective of forming an oleogel that has the sensory and performance characteristics of this disclosure, the following adaptations of the preparation process may be beneficial.

Selection of the starting protein isolate. Beneficial are isolates that may have an initial microstructure of some kind and/or begin to form a microstructure early in the process—such as forming a clear stranded gel referred to in step (3) above.

Optimized conditions for formation of the gel from the denatured protein. Having a fine-stranded nano-structure may impact the morphologies and related physical properties of microstructures in the drying process. Adjusting the pH to between 2 to 4 helps. Other factors affecting structure formation that can be empirically optimized include salt concentration, temperature cycle, timing, and other details of this part of the process.

Optimized freeze channeling. Instantly freezing the gel made from denatured protein helps minimize ice crystal size. Drying the frozen preparation in a vacuum forms microchannels as passageways for water removal. These events promote microstructure formation and consolidation, and preserve microstructures already beginning to form. Spraying the denatured protein into liquid nitrogen and lyophilizing at low pressure is effective. Depending on circumstances, a pellet freezer may be used for scale-up, such as a GEA brand nitrogen freezer.

Incorporating oil into the dried powder gradually with optimized shear. The oleogel imaged in FIG. 1 was obtained by adding oil into the powder dropwise. Possible alternatives for scale-up include spraying, dripping, or otherwise adding oil into the powder and using a paddle mixer to knead, or by tumble mixing. The oil is added to the microstructure with a calibrated (empirically optimized) amount of shearing.

Modes of Combining the Oil with the Protein

In general terms, the mixing of oil into the protein preparation is done in a manner whereby particles of solid protein are lifted into suspension and separated from one another, gently breaking apart particles of the microstructure that are loosely or not structurally interconnected, but without unduly disturbing each of the individual particles once they attain an optimal size and aspect ratio.

The mode of adding the oil to the protein powder can be continuous or discontinuous. For gentle manual or automated paddle mixing methods, partial oil additions are carried out in plurality of tranches, each comprising adding a portion of the oil, and mixing the portion into the oil into the protein before adding more. For example, the combination can be mixed in between each addition for 1 to 5 min, with complete oil incorporation achieved over a total of least 10 or 20 min, up to 30 or 60 min or more. Alternatively, the oil may be dripped, sprayed or flowed into the powder on a continuous basis with continuous or intermittent mixing: for example, over a period of at least 10 or 20 min, up to 30 or 60 min or more.

When using a stirring apparatus, the shape and pliability of the blade is chosen to optimize maintenance of the microstructure. To mix by stirring around a vertical axis, a hydrofoil type blade may provide the gentlest agitation with the least shear. The blade profile creates nearly uniform flow with the minimum rpm and power input, and is especially effective for materials that can be damaged by higher shear. For example, large diameter hydrofoils of one-third of the vessel diameter driven at low rpm may work well. Marine style propellers and axial flow turbine impellers may be used as an alternative. The chosen mixing speed used (in rpm) is slow and gentle, increasing the time required to complete the procedure but lessening impact on individual particles of the microstructure.

Alternatively, when using a tumble mixer, the size of the chamber is chosen to match the lot size of the preparation, decreasing the distance and impact of falling in the downward part of the rotation. Again, the mixing speed (in rpm) is slow and gentle, increasing the time required to complete the procedure but lessening impact on individual particles of the microstructure.

In some circumstances (depending on the protein source and the desired outcome), the protein powder can be added to the oil rather than the other way around. However, this requires that the buoyancy of the dry protein in the oil be overcome, often implying more vigorous mixing, which imposes greater shear. A third alternative is to combine the full amount of oil with the protein in a single step. This is followed by gentle mixing under slow tumbling or gentle flow that helps preserve the microstructure: for example, over mixing times of 10 or 20 min or more.

The mode of mixing is selected from amongst these alternatives and developed empirically to impose an optimized amount of shear, thereby creating an oleogel comprising protein particles dispersed in the oil that have a microstructure with a high aspect ratio. Too much shearing of the protein during oil incorporation will unnecessarily triturate or grind the particles to a smaller median size and rounder shape that is less capable of structuring the oleogel to have desirable oil release properties. Shearing is a function of shear stress and the time over which the shearing is applied. Shear stress depends on the manner of combining the oil into to the powder and the equipment used.

If the dried protein preparation comprises a microstructure that is already mostly in the form of fibrils, sheets, or other particles with a high aspect ratio, the amount if shear is calibrated to minimize impact on individual particles, breaking apart loose interconnections between particles, but without reducing the median diameter of the particles by two-fold or more, or decreasing the median aspect ratio of the particles by two-fold or more. If instead the dried protein comprises a microstructure that is mostly in the form of larger solid, meshed, or honeycombed blocks, the amount of shear is calibrated differently. In this case, the objective is to break apart the blocks of protein in such a way as to generate and maintain particles that have a median size and a median aspect ratio that structures the oleogel to have desirable oil release properties.

Detailed Protocol

FIG. 3B is a flow chart of the current method used at Shiru to prepare oleogels having desirable characteristics and properties. Putting this in terms of a Betty Crocker® style recipe, the procedure is as follows.

Ingredients:
1) protein isolate (for example, potato protein fraction Solanic®300 from Royal Avebe, Veendam, Netherlands)
2) baking soda
3) vacuum bag
4) filtered water
5) food safe liquid nitrogen
6) edible vegetable oil (for example, high oleic acid sunflower seed oil).

Procedure:

Hydration and solubilization: Measure out 190 g of potato protein isolate powder into one or two large containers. Add 2.8 L of filtered water to the protein. Stir at 600 rpm on a magnetic stir plate with a large magnetic stir bar for at least 20 min; or until the solution is no longer opaque, with no visible chunks of the protein powder. The resulting suspension will be transparent and tinted brown.

Creating a protein aggregate. Prepare a sous vide (a vacuum pack) of the hydrated protein using, for example, equipment from Annova (Lewis, Delaware). This is done as follows: dress a sous vide container in a jacket to decrease heat losses during the temperature ramp and gelation cycle. Fill the sous vide container to 9 to 10 quarts of liquid. Set the temperature to 92° C., and begin preheating.

Adjust the pH of the hydrated protein to 4 by adding baking soda, monitoring with a calibrated pH probe. The baking soda is added in in small (<0.5 g) increments, allowing about two min between each addition for the pH to equilibrate. Once the pH has been adjusted and stabilized, pour the acidified protein mixture into sous vide vacuum bags, and seal using the vacuum sealer. This typically generates five bags of about 500 mL each.

Place the bags in the heated liquid in the sous vide container. Start timing when the liquid reequilibrates to 92° C. (the gelation temperature). Maintain at this temperature for 30 min. Then remove the sous vide bags from heat, and immerse the bags in ice cooled water for 10 to 20 min. A clear stranded gel will form.

Creating a high shear mix: Combine clear gels from the sous vide bags in a cambro (or other large plastic food safe container). Add 500 mL of filtered water to the gel mass. Begin shearing with a high shear mixer or an immersion blender (such as a Breville Control Grip Immersion Blender, combined with an overhead stirrer such as the IKA Microstart set to at least 10,000 rpm). The resulting solution will be homogenous throughout. It will appear opaque due to incorporation of air pockets upon mixing. If a foam forms on top, allow time for the foam to settle.

Flash freezing in liquid nitrogen (LN2). Clean and rinse a mister spray apparatus (such as a HeritageQ™ brand Food Grade mister) with a food safe sanitizing solution and water. Fill a cryogenic container with liquid nitrogen. Spray the high shear protein mix directly into the liquid nitrogen, while breaking ice clumps that may form using a strainer. Once the container is full, collect frozen beads using a mesh, and pour the beads into labeled containers. Repeat spraying and collecting as necessary. The frozen beads may be stored at this point, or placed directly into freeze dryer trays.

Freeze drying/lyophilization: Load the frozen material from the preceding step into trays, and place them in the lyophilization apparatus (such as a Harvest Right freeze dryer). Begin the drying cycle. When samples reach room temperature, and the pressure is lower than 200 MT, remove the dried protein from the freeze dryer. Disperse into a powder if necessary. Moisture at this stage should typically be no more than about 5 percent.

Oil incorporation: Delicately place the freeze-dried protein into large beakers or cambro. Begin to add the oil gradually, stirring between additions with a paddle or rubber spatula. Combine by performing multiple tranches or cycles of adding oil into the powder, and mixing between each addition. For example, add about 25% of the oil at a time, using smaller amounts towards the final addition. Alternatively, the oil can be added to the protein gradually by dripping or spraying with continual mixing. To produce oleogel having the microstructure shown in FIGS. 1A and 1B, the oil was added discontinuously with mixing in between of 1 to 5 min, for a total time to complete the combining of between 10 and 30 min.

Knead the final mixture (for example, by hand or using a rubber spatula) until the mass is homogenous. This forms an oleogel dough with no visible heterogeneity of dryness or oiliness.

Nature of the Protein Isolate Used to Make the Oleogel

The physical and sensory data provided in in this disclosure were obtained from oleogels made using Solanic® 300. This is a particular isolate fraction produced from potatoes by Royal Avebe in the Netherlands. Other protein isolates can be tested as an alternative. One or a plurality of criteria selected from the following list are beneficial:
  high solubility (well over 5% wt/vol) in low ionic strength aqueous buffers or pure water. Isolates having a low median mol. wt or that have been hydrolyzed tend to be more soluble;
  consistent (lot-to-lot) higher-order protein structure for robust and reproducible heat-onset aggregation and gelation;
  an appropriate isoelectric point (pI) so that the protein remains soluble during the low pH denaturation step;
  when heated, the protein forms a clear, fine-stranded and relatively homogeneous hydrogel network.

High aqueous solubility in the relevant processing conditions facilitate formation of relatively homogeneous clear gel intermediates, which may subsequently yield relatively homogeneous protein structures and oleogels with superior texture and oil-holding characteristics.

As an alternative to mixed protein isolates, some aspects of this disclosure can be implemented using a recombinantly expressed protein or mixture thereof as the principal source of protein, or as an additive. U.S. Pat. No. 11,439,159 (Hume et al., Shim Inc.) provides information on how to select individual proteins with a target function, and how to express and test the selected proteins.

In the event that a chosen protein or protein isolate does not spontaneously form a microstructure that gives the oleogel a desired oil release profile, the user may include additional steps to promote the formation of particles with a high aspect ratio.

For example, the solubilized or suspended protein may be treated to promote crosslinking between smaller particles before the solution or suspension is flash frozen and dried. Suitable agents include the enzyme transglutaminase, which catalyzes protein crosslinking between glutamyl and lysyl residues in the protein, and certain oxidative enzymes. Other potentially suitable enzymes include laccase, tyrosinase, and peroxidase. M. Motoki et al., Trends Food Sci Technol 9(5):204-210, 1998; N. S. Sulaiman et al., Int Food Res J 29(4):723-739, 2022. The amount of crosslinking agent and reaction time are titrated so that the protein in the preparation forms a loose association of particles of an appropriate size, which can then be dispersed optimally during the oil incorporation phase.

Formation of fibrils and related structures can also be promoted by adding additional components to the protein preparation at an appropriate time during the procedure. For example, a maltodextrin or other polysaccharide can be used to create a glycoconjugate in the form of fibers, optionally by applying a physical process such as needleless ultraspinning M Gibis et al., Appl. Sci. 2021, 11:7896-7909.

Nature of the Oil Used to Make the Oleogel

The oil phase of the oleogel can be any type of oil or a blend of oils suitable for the intended purpose. For use in foods, cosmetics, and pharmaceuticals, the oil will be suitable for human consumption. In this context, the oil is typically a mixture of fatty acids and/or fatty acid esters wherein the lipids are primarily saturated, monounsaturated, polyunsaturated, or a combination thereof, and typically not hydrogenated. Examples of suitable oils include canola oil, soybean oil, sunflower oil, olive oil, palm oil, and coconut oil. Suitable oils for personal care products may or may not be characterized as edible, as long as they are safe when ingested or topically applied on frequent occasions. Different oils may pack differently, which in turn may affect the properties of the oleogel product.

Physical properties and/or sensory properties of an oleogel of this disclosure can be altered and optimized empirically by testing and selecting from a variety of starting protein isolates, by testing and selecting the oil, by adjusting the protein to oil ratio, and by adjusting the method of preparation. In principle, the oleogel can be formulated to have a range of desired properties and consistency, from a soft smooth consistency (for example, for use in spreadable foods and cosmetics), to a firm consistency that releases oil or stays solid when cooked (for example, for use in plant-based meat substitutes).

Assessing Microstructure of Protein Oleogels and Intermediates

The superior oil retention and release properties of the oleogels of this disclosure are believed to be a function of the microstructure embedded in the oil. The solid microstructures of some of the previous protein oleogels results in the oleogel being hard, unspreadable, and resistant to releasing the oil upon heating or shearing. The pebble or granular microstructures of some of the previous protein oleogels results in the oleogel liquifying at low temperature, and being unstable upon storage or when emulsified in water. Oleogels having a microstructure of larger particles will often be gritty and have an unsatisfactory mouthfeel.

FIG. 5 quantifies some of the features that can be seen in the micrographs shown in FIG. 1. The fibrils shown in insets A1, A2, A3, and A4 (left) were characterized by outlining resolved edges of the structures (center) and representing their features in a line drawing (right). Measurements were taken using a pixel-to-micron conversion derived from the embedded 20 μm scale bar. The selected structures are micron-scale protein tubes, fibers, or ribbons with a characteristic diameter or thickness (T) defining their narrowest dimension, which ranges from 0.5 to 5, typically 1 to 3 microns.

Some of the fibrils in this preparation constituted a single linear segment with a defined length (L). Other fibrils were more complex structures comprising several linear segments of length (L) joined at branch points (indicated by circles in the line drawing). The maximum length (ML) of each branched structure was calculated here as the sum of the length of its most parallel linear segments, which ranged from 10 to 100 μm. to be larger than 10 microns. The aspect ratio (AR) of each microstructure was calculated as its maximum (ML) length divided by its diameter or thickness (T). Aspect ratios as high as 10 to 100 were frequently observed.

The sheet-type structures shown in insets B1, B2, B3, and B4 were irregular plates, having a characteristic width (W) and height (H) determined as the longest apparent axes of an idealized two-dimensional polygonal structure. In this preparation, W and H ranged from 10 to 100 microns. The thickness (T) of a plate is assumed to be no larger than the thickness of fibrils observed in the same preparation or micrograph: in this instance, about 1 to 3 (average of 2) microns. Plates may or may not have one or more associated or embedded fiber, tube, or ribbon-like features. Such features are suggested by the coincident termination at the edges of the larger continuous structure. Plate to plate interconnections ("ridges") or plate to fibril interconnections ("seams") often extended along the width or height of a plate. These extended interconnections are indicated in insets B1, B2, B3, and B4 as dotted lines. Each of the plates may be flat, bucked, or folded.

The high aspect ratio (due to the low thickness of the fibrils or sheets) helps to maximize the effective oil absorption capacity of the micro structurant (the oil to protein ratio), while maintaining a semi-solid, lubricating system that lacks the grit associated with dispersing low aspect ratio protein particles in oil.

The percentage of total protein or denatured protein in the preparation that is in the microstructure is typically 20% to 100%, with higher percentages (40%, 60%, or more) representing a more efficient use of the protein content for structuring and stabilizing the oil. Additional protein, carbohydrate, or other components may be included, for example, to catalyze or promote formation of the microstructure, to stabilize or preserve the oleogel during storage, as a pharmaceutical ingredient, and/or to increase nutritional value.

Ratio of protein to oil (wt/wt) are typically 2:98 to 40:60. Ratios at or above 25:75 will generally be less creamy, and accordingly will be less desirable in many contexts. Lower ratios (5:95, or 3:97 to 10:90) are generally more efficient use of the protein and therefore more cost effective in food production. Lower ratios are also appropriate for use with highly saturated oils, such as coconut oil and palm oil used in baking, and mango butter used in cosmetics. Saturated oils generally are solid or semi-solid at room temperature, but may benefit from incorporation into an oleogel to improve melting and/or oil retention characteristics.

Assessing Physical Properties of Oleogels and Intermediates

Besides microstructure, protein oleogels can be assessed by physical criteria. This enables the user to compare oleogels made via modified procedures, and iteratively adjust the process and reassess the oleogels obtained thereby.

FIG. 4 is a melt curve that compares the behavior of coconut oil with two preparations of protein oleogel (determined each in duplicate). Traditional (non-protein) oleogels are commonly able to hold onto oil but don't release it, resulting in a material that is waxy or plastic-like in consistency. In plots of this type, this would show as a mostly horizontal line near the top. Protein oleogels having a rigid mesh or honeycomb structure would show the same sort of horizontal melt curve. In contrast, unstructured coconut oil melts completely at low temperatures, showing as a steeply descending curve that goes to zero. Protein oleogels having a meshwork that consists mostly of pebble shapes or other small particles would show a similar melt curve.

The oleogels of this disclosure achieve a happy compromise. They are pliably solid or spreadable at room temperature, and release oil upon heating and/or shearing. Curves for several oleogel preparations in FIG. 4 are downward sloping, showing release of a substantial proportion of oil they contain at typical cooking temperatures. The curves do not descend all the way to zero, because not all of the oil is released. There was some residual protein material after-heating to cooking temperature (160° C. 320° F.).

Oleogel texture can be objectively measured using an analysis apparatus such as the AMETEK™ Brookfield CTX texture analyzer. Texture profile analysis (TPA) is done via a double compression test to 50% deformation at 0.5 mm per sec. using a 5 kg load cell. The readout is the peak force during first compression reported in Newtons (N). Total work (mJ), chewiness (N), gumminess (N), springiness, cohesiveness, and adhesiveness (mJ), can also be determined. Hardness tends to be the most differentiating measurement. Oleogels can also be characterized according to the effect on viscosity at room temperatures or upon heating.

Assessing Emulsifying Properties of Protein Oleogels

Emulsifying properties were determined at several stages during the oleogel production process. The relative proportions of oil, water, and protein were maintained for all samples. A solution of native potato protein foamed but did not form a stable emulsion and separated quickly. A gelled potato protein solution showed some ability to emulsify, but a substantial portion of free oil remained, and the mixture separated into two phases. However, microparticulated protein obtained after denaturing and freeze drying produced a firm, stable, bright white emulsion.

The protein oleogels of this disclosure create stable emulsions without the need for additional stabilizers. At overall use rates of 40 to 60%, the oleogel can be combined with water using medium to high shear. The oil-in-water emulsion formed thereby is stable for at least four or eight weeks at ambient temperature, with no evidence of phase separation.

Emulsions may be destabilized by any one of four different mechanisms: creaming or sedimentation, flocculation, coalescence, and Ostwald ripening. Creaming occurs when the emulsion separates due to a density difference where the lighter oil droplets rise to the surface. Sedimentation follows the same mechanism but occurs typically in water-in-oil emulsions where denser water droplets accumulate on the bottom of the emulsion. Creaming or sedimentation can be hindered by having a high viscosity continuous phase. Flocculation occurs when the emulsion droplets aggregate and thereby form larger units. Coalescence occurs when smaller droplets merge together forming a larger droplet. This results from droplets coming in contact with each other, rupturing the interfacial film and leading to phase separation. Ostwald ripening occurs when the smaller drops first dissolve in the continuous phase, and then coalesce into larger drops to reach thermodynamically more stable state. The oleogels of this disclosure are resistant to all such forms of destabilization.

Assessing Sensual Properties of Oleogels

Sensory properties of oleogels can be assessed systematically while still essentially a composition of protein and oil. A standardized method for assessing lubricity, smoothness, hardness, and adhesiveness is as follows. The determination is done by human volunteers using thumb and index fingers. TABLE 3 outlines the protocol.

TABLE 3

Subjective tests for sensory attributes of fats, oils, and oleogels

| Attribute | Definition | Method to test | Low benchmark (scale value) | High benchmark (scale value) |
|---|---|---|---|---|
| Hardness | Force required to push into a sample | Gently press with index finger | Lard (1) | Tallow (5) |
| Lubricity or oiliness | Ability to reduce friction. Slippery, amount of liquid oil | Rub oleogel between index finger and thumb until melted | Tallow (3) | Coconut oil (5) |
| Smoothness | Opposite of gritty, has a smooth texture, it does not feel grainy or sandy when rubbed or spread | Rub oleogel with thumb and index finger and feel the number or size of particles | Lard (3) | Coconut oil (5) |
| Adhesiveness/ Stickiness | How the sample adheres to a surface | Place sample between thumb and index finger and separate. Higher resistance means higher stickiness | Coconut oil (1) | Tallow (2.5) |

FIG. 6A shows the five-point scale for each of the four values. Each scale is benchmarked using lard, butter, shortening, coconut oil, and tallow, as shown. For a protein oleogel preparation prepared according to the protocol set forth above, the values were as follows: Hardness=2, lubricity=4.5, smoothness=5, adhesiveness=1. These values are especially appropriate for food preparation: the oleogel preparation tested here is not hard or sticky, but is smooth and lubricating.

FIG. 6B presents the test data as a spider plot. The solid line marked "Shiru oleogel 1" was made by the optimized process outlined above. The high values for lubricity and smoothness are prominent. The line with sort dashes marked "Shiru oleogel 2" was an early product made with a different process that did not include pH adjustment, denaturation, or immersion blending.

FIG. 7 is a flowchart suitable for iteratively and empirically optimizing process control variables (right column) by measuring sensory properties using internal benchmarks (left column) and material properties (middle column).

Assessing Properties of Foods Made with Protein Oleogels

The sensory properties of oleogels can also be determined systematically when combined with other ingredients in the manner of food preparation. Products made using different oleogel preparations can be compared with each other and with products made with more traditional structured fats and oils.

A protein oleogel made according to the protocol put forth above was compounded into a cooked patty. The ingredients are listed in TABLE 4. In this sort of test, use of a flavoring agent is optional. Flavoring was not used here, so that the volunteer test subjects could focus on texture and other subjective features.

TABLE 4

Ingredients for test patties

| Ingredient | Percent (wt/wt) |
|---|---|
| Textured pea protein (TVP) | 19 |
| Salt | 0.8 |
| Water | 38 |
| Methylcellulose | 1.5 |
| Soy protein isolate | 3 |
| Fat (oleogel or other oil) | 15 |
| Water | 19 |
| Cornstarch, native | 3 |

The procedure for preparing the patties was as follows: Soak TVP in first portion of water and salt for 30 min. Disperse methylcellulose and soy protein in melted coconut oil, and add additional water to form an emulsion. Add cornstarch and emulsion to soaked TVP and mix until incorporated. Cool at 40° F. for 2 hours. Form into 25 g patties and bake at 375° F. for 14 min.

Two controls were prepared with an oil instead of the oleogel. The positive control was 15% coconut oil, and the negative control was 5% coconut oil baked for an additional 8 min.

FIG. 8A are graphs of the cooking loss (percent weight loss after baking) and hardness. The hardness was assessed using a Brookfield CTX texture analyzer at 40% compression, internal temperature of 50-70° C. Patties made with oleogel were compared with two controls: patties made instead with 15% coconut oil, (the positive control), and patties made with just 5% coconut oil, baked for an additional 8 min (the negative control). Compared with the positive control, the oleogel reduced cooking loss from an average of 17% to 13.6%. The hardness of the oleogel (5.5 N) was comparable with hardness of coconut oil (6.3 N).

FIG. 9 shows a scale used to evaluate the patties by sensory criteria. Qualitative descriptive analysis (QDA) was done using a panel of 24 trained volunteers to assess burger patties for firmness, juiciness, and fattiness. The test was done blinded, so the panel members did not know which of the patties were made with the oleogel, and which were made with coconut oil. Each of the criteria were benchmarked using other products. Benchmark patties were made with oleogel, or with low (5%, Shim B), medium (15%, Shiru A), and high (20%, Shim C) levels of coconut oil.

FIG. 8B shows the results. Firmness, juiciness, and fattiness scores for patties made with oleogel ("Shim alt fat") were assessed by the panel as similar to the positive control. There was a significant difference from the negative control, demonstrating the sensitivity of the responses.

Visual Appearance of Protein Oleogel and Products Made with the Oleogel

FIG. 10 shows the spreadable texture of a preparation of protein oleogel as manufactured according to this disclosure. This is anhydrous oleogel: it looks more like a cream but isn't wet. When mixed with water, the oleogel forms an emulsion that is shinier and has softer edges.

d FIG. 11 compares the cooking of test patties made with coconut oil or with protein oleogel. The oil melted and bubbled away from the patty made with coconut oil. In contrast, oil in the oleogel patty mostly stayed within the patty.

FIG. 12 shows protein oleogel incorporated into meat replacement products with fat regions separated from protein regions. These samples were made by blending tofu with protein, starch, and color to form the lean meat portion of bacon. This was layered with the oleogel into a block that was frozen, sliced, and pan-cooked.

Commonly Used Fats and Oils in Foods that can be Replaced with Oleogels

The oleogels of this disclosure can be used mutatis mutandis to replace structured fats and oils, especially those that are solid, semisolid, or spreadable at room temperature, but transition to something softer when heated: For example, beef tallow, pork back fat, lard, other meat rendered fats and extracts, coconut oil, palm oil, hydrogenated oil, margarine, other types of shortening, and butter.

Food Products Incorporating Oleogels

The oleogels of this disclosure can be used any food product that currently has a substantial oil and/or fat content. Protein oleogel may be used as a partial or complete substitute for animal fats, for fats that are considered nutritionally unsatisfactory, or for fats that are difficult or expensive to produce. Alternatively, the user may wish to use the oleogel in a food product simply because the oleogels of this disclosure have superior properties. Any of the foods listed in TABLE 1 above can be prepared using an oleogel according to this disclosure in place of the oleogel specified in the cited reference.

Incorporation of oleogels into a food product or preparation method may be empirically optimized by the user. As a guide, the user may wish to start by adapting a known recipe or manufacturing process for a particular processed food product by replacing entirely or in part one or more oils, fats, or oily structures in the recipe or process with roughly an equal or equivalent mass of oleogel. For foodstuffs such as marbled meat or bacon, the process may involve seeding a scaffold structure with pockets of meat-like protein and meat-like fat to visually and textually mimic the animal product.

The user may incorporate oleogels into food products at a mass ratio that is appropriate for the optimal texture they require. This will depend on the other ingredients in the product, whether the product will be heated, and the particular protein oleogel in use.

In general, any concentration of between 1% and 90% wt/wt of dry food ingredients may be suitable. A range of 3% or 5% to 80% is more typical. Typical working ranges for various types of food products are as follows:

plant-based ground meat replacement: 4 to 25% wt/wt of product formulation;
vegan cake: 10 to 25% wt/wt;
dairy products: 2 to 50%;
whipped topping: 15 to 45%.

The following recipes illustrate how the protein oleogel preparations of this disclosure can be used to make plant derived replacement foods for meat products, sausages, and nuggets, and for cake, cookies, and ice cream.

Plant Based Beef-Like Products

Meat replacement preparations can be made from plant components by combining 60% (wt/wt) muscle replica, about 30% (wt/wt) fat tissue replica, and about 5% (wt/wt) connective tissue replica. U.S. Pat. No. 10,863,761. Muscle tissue replica can be made by combining a heme binding protein such as myoglobin or leghemoglobin (12 mg/mL) with about an equal volume of plant protein (150 mg/mL) in the presence of a crosslinking agent such as transglutaminase (about 1 wt/vol). Fat tissue replica can be made from seed or pea globulin by combining with an oil such as soy or rice bran oil in the presence of transglutaminase by heating at ~95° C. for 5 min and then cooling. It typically forms an opaque gel off-white in color, smooth uniform texture, with no visible discernible liquid that was not incorporated into the gel. Connective tissue replicas can be prepared as a combination of plant proteins or structural equivalents that mimic collagen or fascia like fibers, or a combination of the two.

The meat replacement preparation may also contain a sugar and/or a sulfur-containing compound that is not part of a protein. The sugar may be selected from glucose, ribose, fructose, lactose, xylose, arabinose, glucose-6-phosphate, maltose, and galactose, and mixtures of two or more thereof. The sulfur-containing compound may be selected from cysteine, cystine, selenocysteine, thiamine, methionine, and mixtures of two or more thereof. Meat-like flavor or aroma may be manifest during cooking, which results in release of at least two volatile compounds with a meat associated aroma, selected, for example, from 2-methyl-furan, bis(2-methyl-3-furyl)disulfide, 2-pentyl-furan, and so on.

Preparation and features of some meat replacement compositions is outlined in U.S. Pat. Nos. 3,814,823; 9,700,067; 10,863,761; 10,798,958; and 11,013,250; and in EP 3952661 A1. An illustration is shown in Table 5A.

TABLE 5A

Ingredients for plant-based beef replacement foods

| Ingredients (% wt/wt) | |
|---|---|
| textured pea protein | 16-20% |
| beef-type flavor and color | 1-4% |
| salt | 0.8% |
| water | 48-60% |
| methylcellulose | 1.5% |
| soy protein isolate | 3.0% |
| fat (Shiru alt fat or coconut oil) | 12-18% |
| cornstarch | 3.0% |

Directions for burger patties: Mix water-soluble flavors and colors with water. Soak the TVP in this for one hour. Mix in dry ingredients, then incorporate fat to form a dough. Chill for one hour. Form the dough into 50 g portions and shape into patties. Cook in oven at 375° F. for 17 min, or in a non-stick pan at 400° F., 5 min per side.

Directions for plant-based meat-like meatballs: Prepare the dough as for the patties. If desired, add additional flavor components such as onion, garlic, and parsley. Divide into 25 portions, and shape into balls. Bake at 375° F. for 15 min.

Sausages

TABLE 5B

Ingredients for sausages

| Ingredients (% wt/wt) | |
|---|---|
| water | 48-60% |
| texturized vegetable protein (TVP) | 16-20% |
| oleogel | 14-20% |
| water | 38% |
| texturized vegetable protein (TVP) | 16% |
| oleogel | 17% |
| fava bean protein | 5% |
| beet powder | 0.5% |
| garlic powder | 0.9% |
| nutritional yeast | 0.9% |
| dried onion | 0.1% |
| cocoa powder | 0.3% |
| ground thyme | 0.1% |
| white pepper | 0.2% |

TABLE 5B-continued

Ingredients for sausages

| Ingredients (% wt/wt) | |
|---|---|
| malt vinegar powder | 1.3% |
| salt | 1.1% |

Directions: Make sausage binder by mixing methylcellulose or other gelling agent with water until completely dissolved. Weigh and combine dry and liquid ingredients separately. Mix dry and liquid ingredients together using a standing mixer at medium speed. Let the dough hydrate for 20 min at room temp. Using a sausage filler attachment on the stand mixer, fill vegetarian casings with the dough. Pan-fry at 400° F. until internal temperature reaches 165° F., rotating occasionally to brown all sides.

Plant-Based Chicken Nuggets

TABLE 5C

Ingredients for chicken-like nuggets

| Ingredients (% wt/wt) | |
|---|---|
| water | 57% |
| texturized vegetable protein (TVP) | 17% |
| potato starch | 13 to 18% |
| baking powder | 2.5% |
| methylcellulose | 1 to 5% |
| salt | 0.3% |
| calcium chloride | 0.2% |
| oleogel | 3.5% |

Directions: Prepare dough by mixing all ingredients in a food processor for 5 min at low speed. Mold and shape into nuggets. Steam at 210° F. for 14 min Make batter by combining flour and water in a 1:2 ratio. Coat the nuggets with the batter. Deep fry for 1 V2 min, then freeze. To prepare for consumption, bake the frozen nuggets at 425° F. for 15 min.

Vegan Vanilla Cake

TABLE 5D

Ingredients for cake

| Ingredients (% wt/wt) | |
|---|---|
| apple cider vinegar | 1.3% |
| unsweetened plant-based milk (coconut, almond, oat, or soy) | 31 to 34% |
| all-purpose flour | 21 to 26% |
| sugar | 22% |
| baking powder | 0.8% |
| baking soda | 0.3% |
| salt | 0.6% |
| oleogel | 11% |
| vanilla extract | 2.1% |
| egg replacer solution (2:1 water and flax meal mixture) | 8 to 12% |

Directions: Preheat oven to 350° F. Hydrate egg replacer solution in water (between 1.5% and 8%, as appropriate). Combine vinegar and milk or milk replacement, and let stand for 5 min Combine flour, sugar, baking powder, baking soda, and salt. Add fat, vanilla, and protein solution to the milk mixture. Combine liquid and dry ingredients. Pour batter into an oiled 8-inch cake pan lined with parchment paper. Bake for 36 to 38 min, or until golden brown and set in the center. Let cool to room temperature.

Cookies

TABLE 5E

Ingredients for cookies

| Ingredients (% wt/wt) | |
| --- | --- |
| flour | 25% |
| salt | 0.3% |
| baking soda | 0.3% |
| oleogel | 15% |
| sugar | 20 to 23% |
| egg replacer solution (2:1 water and flax meal mixture) | 12 to 18% |
| vanilla extract | 0.9% |
| vegan chocolate chips | 26% |

Directions: Preheat oven to 350° F. Hydrate egg replacer solution and vanilla extract. Mix until well combined. Add flour, salt, and baking soda. Add chocolate chips. Separate into 100 g portions. Shape into balls, and place on a cookie sheet. Bake for 18 to 21 min Plant-Based Ice Cream

TABLE 5F

Ingredients for plant-based ice cream

| Ingredients (% wt/wt) | |
| --- | --- |
| water | 55% |
| soymilk powder or pea protein concentrate | 4.4% |
| texturized vegetable protein (TVP) | 8% |
| oleogel | 8% |
| sweetener (sugar or syrup) | 23% |
| tapioca solids | 2 to 5% |
| stabilizers or gelation agent | 0.2 to 3% |

Directions: Mix soy milk or pea protein powder with water in a saucepan. Heat to between 110° F. and 125° F., stirring constantly. Incorporate the rest of the ingredients while stirring constantly. Homogenize ingredients at 15,000 rpm for 3 min. Age at 40° F. for up to 24 hours. Using an ice cream maker, freeze the mixture and incorporate air for 20 min.

Regulatory Approval of Oleogels as Ingredients in Processed Food Products

After a particular oleogel formulation has been identified for further development as a food ingredient, the user will assure that all regulatory requirements are met before beginning commercial distribution. For example, new food additives and products thereof for distribution in the U.S. may be subject to premarket approval by the Food and Drug Administration (FDA). The new additives are "generally recognized as safe" (GRAS) if there is generally available and accepted scientific data, information, or methods indicating it is safe, optionally corroborated by unpublished scientific data. A notification sent to FDA's Office of Food Additive Safety for approval includes a succinct description of the substance (chemical, toxicological and microbiological characterization), the applicable conditions of use, and the basis for the GRAS determination. The FDA then evaluates whether the submitted notice provides a sufficient basis for a GRAS determination.

Use of Oleogels in Cosmetics and Beauty Products

The oleogels of this disclosure can be tested as a replacement for any one or more of the various lubricants, emulsifiers, emollients, and other oily and creamy components that are commonly used as components of cosmetics and personal care products of any kind.

Cosmetics typically contain a combination of the following core ingredients: water, emulsifier, preservative, thickener, emollient, color, fragrance and pH stabilizers. Purified water forms the basis of almost every type of cosmetic product.

Emulsifying agents keep hydrophilic and hydrophobic components of a preparation from separating. Many cosmetic products are based on emulsions—small droplets of oil dispersed in water or small droplets of water dispersed in oil. Emulsifiers are added to change the surface tension between the water and the oil, producing a homogeneous and well-mixed product with an even texture. Emulsifiers frequently used in cosmetics include polysorbates, laureth-4, and potassium cetyl sulfate. Preservatives are added to cosmetics to extend their shelf life and prevent the growth of microorganisms such as bacteria and fungi, which can spoil the product and possibly harm the user.

Thickening agents are used to give products an appealing consistency and facilitate use. Lipid thickeners work by imparting their natural thickness to the formula. Examples include cetyl alcohol, stearic acid and carnauba wax. So-called naturally derived thickeners are polymers that absorb water, causing them to swell up and increase the viscosity of a product. Examples include hydroxyethyl cellulose, guar gum, xanthan gum and gelatin. Mineral thickeners absorb water and oils to increase viscosity, but give a different result to the final emulsion than the gums. Popular mineral thickeners include magnesium aluminum silicate, silica and bentonite.

Emollients soften the skin of the user by preventing water loss. They are used in a wide range of lipsticks, lotions and cosmetics. A number of different natural and synthetic chemicals work as emollients, including beeswax, olive oil, coconut oil and lanolin, as well as petrolatum (petroleum jelly), mineral oil, glycerin, zinc oxide, butyl stearate and diglycol laurate. Coloring agents and pigments are used in many cosmetics to accentuate or alter a person's natural coloring. Mineral ingredients can include iron oxide, mica flakes, manganese, chromium oxide and coal tar. Natural colors can come from plants, such as beet powder, or from animals, like carmine, often used in red lipsticks. The two most common organic pigments are lakes and toners. Fragrances are often added to liquid and cream cosmetics to improve their appeal.

Tallow is an animal product with a long history of being used to soothe and moisturize skin. It is often a component of cosmetics, personal care products, and soap. Tallow is a rendered form of beef or mutton fat, primarily made up of triglycerides, including a combination of saturated, monounsaturated, and polyunsaturated fatty acids. Reformulating cosmetics to remove animal derived materials can include replacement of one or more of components such as tallow, lanolin, squaline, and/or other oils and oil-related chemicals and materials in any combination.

The oleogel will be present in a cosmetic or personal care product typically at a concentration of 0.5% to 80%, 1% to 60%, or 2 to 20% of oleogel by weight of the final product, depending on the nature of the product and the desired properties thereof. This includes but is not limited to personal care products such as creams, lotions, and balms.

Contemplated is a body butter and a mineral sunscreen, having the formulations shown in TABLE 6.

TABLE 6

| Cosmetic formulations | | |
|---|---|---|
| Ingredients (% wt/wt) | Body butter | Sunscreen |
| oleogel | 67% | 76% |
| avocado oil | 33% | |
| aloe vera gel | | 15% |
| powdered zinc oxide | | 8% |
| essential oil (fragrance) | 0.2% | 0.2% |

Potential performance advantages of the body butter include decreased water loss, increased barrier function, activated protein absorption and activation, and an apparent anti-aging effect. Potential performance advantages of the sunscreen include active stabilization, increased water resistance to UV irradiation, and extended bioactive activity. Selection of particular ingredients and the amounts used may be adjusted by the user to generate a product having a desired texture, fragrance, color, stability, washability, moisturizing capability, and other factors.

For example, mango butter is lightweight, non-greasy and non-comedogenic (not pore-clogging). It is antibacterial, can help nourish the acne-prone skin and reduce production of sebum. Mango and shea butter can be adapted for use in cosmetics by incorporating it into an oleogel of this disclosure as part of an oil mixture at a low protein to oil ratio of 2:98 to 5:95 wt/wt.

Regulatory Approval of Oleogels as Ingredients in Cosmetics and Personal Care Products In the context of this disclosure, the term "personal care product" generally means any article intended to be rubbed, poured, sprinkled or sprayed on, introduced into or otherwise applied to any surface or part of the human body for cleansing, beautifying, promoting attractiveness or altering the appearance, and any item intended for use as a component thereof. In the context of this disclosure, the oleogel may be a component of a product or ingredient that is a compounded liquid, cream, gel, emulsion, colloid, powder, or dissolvable solid, optionally used in combination with a dispensing agent or personal care device.

Some personal care products and ingredients are regulated by the Food and Drug Administration as cosmetics. The Federal Food, Drug and Cosmetic Act (FD&C Act) defines cosmetics as "articles intended to be rubbed, poured, sprinkled, or sprayed on, introduced into, or otherwise applied to the human body for cleansing, beautifying, promoting attractiveness, or altering the appearance." Included in this definition are products such as skin moisturizers, perfumes, lipsticks, fingernail polishes, eye and facial makeup preparations, shampoos, permanent waves, hair colors, toothpastes, and deodorants, as well as any material intended for use as a component of a cosmetic product.

Some personal care products and ingredients meet the FDA definitions of both cosmetics and drugs. This may happen when a product has two intended uses. For example, a shampoo is a cosmetic because its intended use is to cleanse the hair. An antidandruff treatment is a drug because its intended use is to treat dandruff. Consequently, an anti-dandruff shampoo is both a cosmetic and a drug, because it is intended to cleanse the hair and treat dandruff. Among other cosmetic/drug combinations are toothpastes that contain fluoride, deodorants that are also antiperspirants, and moisturizers and makeup marketed with sun-protection claims. Such products must comply with the requirements for both cosmetics and drugs.

Use of Oleogels in Pharmaceutical Products

Oleogels described above can be used as part of a pharmaceutical or nutraceutical product, for example, by combining with an effective dose of one or more pharmaceutically active agents or nutritional ingredients, optional components such as a pharmaceutically compatible preservative, and a pharmaceutically or neutraceutically compatible excipient, lubricant, diluent, or packing material. By way of illustration, the product may be in the form of a capsule or a measurable semisolid for oral administration, or a cream or ointment for topical administration. The oleogel will be present at a concentration of 0.5% to 50% or 2 to 20% by weight of the final product. The user may wish to adjust the salt and pH of the product so as to stabilize the oleogel and its role in the composition.

A drug or pharmaceutical product is a composition that contains at least one active agent that requires regulatory approval and provides pharmacological activity or other direct effect in the diagnosis, cure, mitigation, treatment, or prevention of disease, or to affect the structure or any function of the body of man or animals. A nutraceutical product is any substance or ingredient that is promoted as providing a health benefits, but not regulated by the Food and Drug Administration in the U.S.

FDA approval of a drug requires that the drug's effects have been tested for safety and efficacy in clinical trials or their equivalent, and reviewed by the FDA's Center for Drug Evaluation and Research (CDER). The drug is approved if it is determined to provide benefits that outweigh its known and potential risks for the intended population.

Use of Oleogels in Other Industrial Products and Processes

The structured oleogels of this disclosure can be used as substitutes in other manufactured products that comprise solid, semisolid, or structured oils and lubricants.

By way of illustration, oleogels can be used as a component of motor fuels and lubricants; in the print industry for applying to metal print plates to provide a resistance to acid etching; as an additive to the substrate used in polymer banknotes; in the manufacture candles and other solid fuel sources for heat or light production; in lubrication of steam-driven piston engines in locomotives and steamship engines, in which they are resistant to expulsion; in the steel rolling industry to provide the required lubrication as the sheet steel is compressed through the steel rollers; in the lubrication of rifles and other artillery; as a flux for soldering; or in the production and storage of textiles, for example, to strengthen and lubricate yarns mounted on looms and for textile finishing.

Prior Patent Publications

CN 113261594 B (South China Ag. U)—A rice bran protein oil gel.

CN 114190443 A (South China Inst. Technol.)—Preparing an oleogel comprising dispersing protein powder into oil by using a ball milling technology.

EP 3011836 A1 (Sholten) (abandoned)—Protein-stabilized oleogels made by solvent exchange US 2022/0295811 A1 (Sholten)—Procedure for producing a protein oleogel by suspending protein in an oil, then adding water very very very slowly.

U.S. Pat. No. 8,940,354 (Marangoni, Mars Inc.)—Edible oleogel comprising an oil, ethylcellulose and a surfactant.

U.S. Pat. No. 9,655,376 (Ergun, Dow Chemical)—A continuous process for preparing an oleogel from ethylcellulose and an oily feed material U.S. Pat. No. 10,874,115 (Perez Gallardo, Sigma Alimentos)—Edible oleogel comprising an oil or mixture of oils, grease or mixtures of fats, and a structuring agent of a distilled monoglyceride of saturated fatty acid WO 2022/031172 (Camilleri, BFLike BV)—Oleogel made by cross-linking a hydrocolloid of oil and water using protein.

Incorporation by Reference

Each and every publication and patent document cited in this disclosure is hereby incorporated herein by reference in its entirety for all purposes to the same extent as if each such publication or document was specifically and individually indicated to be incorporated herein by reference.

Interpretation and Implementation of this Technology

Although the technology described above is illustrated in part by certain concepts, procedures, information, and working examples, the claimed invention is not limited thereby except with respect to the features that are explicitly referred to or otherwise required. Theories that are put forth in this disclosure with respect to the underlying mode of production, action, and assessment of various products and components thereof are provided for the interest and possible edification of the reader, and are not intended to limit practice of the claimed invention.

While the oleogels described in this disclosure were developed by the inventors and the owner of this technology as oil and fat replacements and lubricants, the products and methods referred to in the claims that follow can alternatively be used in the manufacture of food, cosmetics, and other products as an adjunct for other oils, fats, and lubricants, for any of their beneficial properties for any reason. Discussion in this disclosure about the microstructure of oleogels does not limit the practice of the invention, the compositions of matter, or the methods claimed below except where explicitly stated or otherwise required. For example, oleogels of this invention made by the manufacturing processes put forth herein, or having the beneficial properties put forth herein, may or may not have a particular microstructure. Oleogels of this invention comprising a particular microstructure may or may not be made by a particular process. The reader may use any aspect of the technology put forth in this disclosure for any suitable or desirable purpose.

While the invention has been described with reference to the specific examples and illustrations, changes can be made and substituted to adapt to a particular context or intended use as a matter of routine development and optimization and within the purview of one of ordinary skill in the art, thereby achieving benefits of the invention without departing from the scope of what is claimed below and equivalents thereof.

The invention claimed is:

1. A protein oleogel comprising a protein structurant dispersed in a liquid oil phase,
    wherein the oleogel has a protein-to-oil ratio between 2:98 and 20:80 wt/wt,
    wherein the protein is a substantially denatured plant protein isolate or a substantially denatured plant protein mixture,
    wherein at least 20% of the protein dispersed in the liquid oil phase has a solid microstructure,
    wherein the microstructure comprises particles that have a median size of at least 10 μm in one or two dimensions and a median aspect ratio (length to thickness) of at least 5,
    wherein the particles are substantially free flowing when the oleogel is diluted in vegetable oil by 10-fold (wt/wt).

2. The oleogel of claim 1, wherein the microstructure instills the oleogel with the property of being solid or semisolid at room temperature, and releasing some but not all of the oil when cooked.

3. The oleogel of claim 1, wherein most of the protein in the oleogel is a protein isolate obtained from potato.

4. The oleogel of claim 1, wherein most of the oil in the oleogel is a vegetable oil that comprises mostly monounsaturated or polyunsaturated fatty acids, or a mixture thereof.

5. The oleogel of claim 1, which retains the oil it contains at room temperature, and releases between 20% and 80% of the oil when heated to 160° C.

6. The oleogel of claim 1, which forms an emulsion when combined 1:1 with an aqueous liquid, wherein the emulsion is stable for at least four weeks at room temperature, with no evidence of creaming or phase separation.

7. The oleogel of claim 1, which has a spreadable consistency at room temperature.

8. The oleogel of claim 1, which is an oil or fat replacement that comprises substantially no aqueous liquid.

9. The oleogel of claim 1,
    which is suitable for use in a processed food product at a proportion of at least 5% (wt/wt) of the product.

10. The oleogel of claim 9, wherein the processed food product is a hamburger patty or other meat product, or a plant-based substitute therefor.

11. The oleogel of claim 9, wherein the processed food product is a cheese substitute, an ice cream, a yoghurt, a dessert topping, or a baked product.

12. The oleogel of claim 1,
    which is suitable for use in a cosmetic or personal care product at a proportion of at least 5% (wt/wt) of the product.

13. The oleogel of claim 12, wherein the cosmetic or personal care product is in the form of a cream, ointment, or lotion.

14. The oleogel of claim 1, with oil structuring and release properties that qualify the oleogel as suitable as a replacement for animal fats and tropical oils in food products.

15. A protein oleogel comprising a protein structurant dispersed in a liquid oil phase,
    wherein the oleogel has a protein-to-oil ratio between 2:98 and 20:80 wt/wt,
    wherein the protein is a substantially denatured plant protein isolate or or a substantially denatured plant protein mixture,
    wherein at least 20% of the protein dispersed in the liquid oil phase has a solid microstructure,
    wherein the microstructure comprises at least 20% fibrils and/or sheets that are substantially not interconnected,
    wherein the fibrils have a median size that is at least 20 μm in length but less than 4 μm in diameter, and the sheets have a median size that is at least 10 μm in length and width but less than 2 μm in thickness.

16. The oleogel of claim 15, wherein the microstructure comprises said fibrils.

17. The oleogel of claim 15, wherein the microstructure comprises said sheets.

* * * * *